United States Patent
Kulas et al.

(10) Patent No.: US 12,064,126 B2
(45) Date of Patent: Aug. 20, 2024

(54) SURGICAL BURS WITH LOCALIZED AUXILIARY FLUTES

(71) Applicant: Medtronic Xomed, Inc., Jacksonville, FL (US)

(72) Inventors: John W. Kulas, Euless, TX (US); Donald E. Stearns, Fort Worth, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 427 days.

(21) Appl. No.: 17/029,437

(22) Filed: Sep. 23, 2020

(65) Prior Publication Data

US 2021/0000488 A1    Jan. 7, 2021

Related U.S. Application Data

(63) Continuation of application No. 15/966,778, filed on Apr. 30, 2018, now Pat. No. 10,786,266, which is a continuation of application No. 14/674,002, filed on Mar. 31, 2015, now Pat. No. 9,955,981.

(51) Int. Cl.
*A61B 17/16* (2006.01)
*A61B 17/00* (2006.01)

(52) U.S. Cl.
CPC ...... *A61B 17/1695* (2013.01); *A61B 17/1615* (2013.01); *A61B 17/1617* (2013.01); *A61B 2017/00544* (2013.01)

(58) Field of Classification Search
CPC ....................................... A61B 17/16–17/1697
See application file for complete search history.

(56) References Cited

U.S. PATENT DOCUMENTS

| | | | |
|---|---|---|---|
| 180,554 | A | 8/1876 | Cubberley |
| 372,400 | A | 11/1887 | Browne |
| 872,400 | A | 11/1887 | Browne |
| 533,573 | A | 2/1895 | Wilkens |
| 533,673 | A | 2/1895 | Wilkens |

(Continued)

FOREIGN PATENT DOCUMENTS

| | | |
|---|---|---|
| CN | 101745679 A | 6/2010 |
| CN | 201565651 U | 9/2010 |

(Continued)

OTHER PUBLICATIONS

Office Action mailed Sep. 11, 2020 in corresponding/related European Application No. 16763164.7.

(Continued)

*Primary Examiner* — Zade Coley
(74) *Attorney, Agent, or Firm* — Carter, DeLuca & Farrell LLP

(57) ABSTRACT

A surgical bur including primary flutes and auxiliary flutes. The primary flutes include (i) first clearance surfaces, and (ii) first rake surfaces with first cutting edges. The primary flutes extend from a proximal end of the surgical bur to a distal end of the surgical bur. The auxiliary flutes are localized in central regions or distal regions of the surgical bur. The auxiliary flutes include (i) second clearance surfaces, and (ii) second rake surfaces with second cutting edges. At least one of the auxiliary flutes is located between a pair of adjacent ones of the primary flutes.

16 Claims, 15 Drawing Sheets

(56) References Cited

U.S. PATENT DOCUMENTS

| | | |
|---|---|---|
| 662,349 A | 11/1900 | Burton |
| 1,309,706 A | 7/1919 | Taylor |
| 2,795,979 A | 6/1957 | Zerwick |
| 2,847,885 A | 8/1958 | Wagner |
| 2,847,895 A | 8/1958 | Wagner |
| 2,903,922 A * | 9/1959 | Ernst .................. B23B 51/02 |
| | | 408/230 |
| 3,387,511 A | 6/1968 | Ackart, Sr. |
| 3,387,554 A | 6/1968 | Cherre |
| 3,872,594 A | 3/1975 | Gerteisen |
| 3,937,222 A | 2/1976 | Banko |
| 4,445,509 A | 5/1984 | Auth |
| 4,594,034 A | 6/1986 | Maier |
| 4,600,006 A | 7/1986 | Baker |
| 4,602,900 A | 7/1986 | Arpaio, Jr. et al. |
| 4,699,550 A | 10/1987 | Baker |
| 4,740,121 A | 4/1988 | Arnold |
| 4,803,982 A | 2/1989 | Baker |
| 4,830,000 A | 5/1989 | Shutt |
| 4,951,690 A | 8/1990 | Baker |
| 4,975,003 A * | 12/1990 | Hosoi .................. B23B 51/02 |
| | | 408/230 |
| 4,978,350 A | 12/1990 | Wagenknecht |
| 5,007,911 A | 4/1991 | Baker |
| 5,011,342 A | 4/1991 | Hsu |
| 5,122,134 A * | 6/1992 | Borzone ............. A61B 17/164 |
| | | 407/30 |
| 5,143,490 A | 9/1992 | Kopras |
| 5,190,548 A | 3/1993 | Davis |
| 5,209,612 A | 5/1993 | Kish |
| 5,236,291 A | 8/1993 | Agapiou et al. |
| 5,302,059 A | 4/1994 | Fabiano |
| 5,336,673 A | 8/1994 | Moon et al. |
| 5,429,504 A | 7/1995 | Peltier et al. |
| 5,467,837 A | 11/1995 | Miller et al. |
| 5,514,141 A | 5/1996 | Prizzi, Jr. |
| 5,575,650 A | 11/1996 | Niznick et al. |
| 5,579,185 A | 11/1996 | Tsai et al. |
| D378,780 S | 4/1997 | Shuler |
| 5,618,293 A | 4/1997 | Sample et al. |
| 5,658,305 A | 8/1997 | Baker |
| 5,759,185 A * | 6/1998 | Grinberg .................. B23C 5/28 |
| | | 606/180 |
| 5,810,517 A | 9/1998 | Bostic |
| 5,833,402 A | 11/1998 | Martin |
| 5,846,035 A | 12/1998 | Karafillis et al. |
| 5,855,581 A | 1/1999 | Koblish et al. |
| 5,860,773 A | 1/1999 | Blomberg et al. |
| 5,913,867 A | 6/1999 | Dion |
| 5,964,553 A | 10/1999 | Blomberg et al. |
| 5,980,525 A | 11/1999 | Bryant et al. |
| 6,068,632 A | 5/2000 | Carchidi et al. |
| 6,132,448 A | 10/2000 | Perez et al. |
| 6,238,398 B1 | 5/2001 | Lechot |
| 6,258,093 B1 | 7/2001 | Edwards et al. |
| 6,332,886 B1 | 12/2001 | Green et al. |
| 6,431,801 B2 | 8/2002 | Vasudeva et al. |
| 6,435,780 B1 | 8/2002 | Flynn |
| 6,511,493 B1 | 1/2003 | Moutafis et al. |
| 6,514,258 B1 | 2/2003 | Brown et al. |
| 6,547,495 B2 | 4/2003 | Meece et al. |
| 6,562,046 B2 | 5/2003 | Sasso |
| 6,579,298 B1 * | 6/2003 | Bruneau ......... A61B 17/320758 |
| | | 606/159 |
| 6,682,349 B1 | 1/2004 | Logeart |
| 6,783,533 B2 | 8/2004 | Green et al. |
| 7,520,703 B2 * | 4/2009 | Rompel .................. B23B 51/02 |
| | | 408/230 |
| 7,862,263 B2 | 1/2011 | van Iperen |
| 8,414,228 B2 | 4/2013 | Wells et al. |
| 8,460,298 B2 | 6/2013 | O'Donoghue |
| 8,852,222 B2 * | 10/2014 | O'Sullivan ...... A61B 17/32002 |
| | | 606/180 |
| 9,179,923 B2 | 11/2015 | Gubellini et al. |
| 9,232,952 B2 * | 1/2016 | Kulas ................ A61B 17/1615 |
| 9,526,508 B2 * | 12/2016 | Burke ..................... B23C 5/10 |
| 9,883,873 B2 | 2/2018 | Kulas et al. |
| 9,924,952 B2 | 3/2018 | Kulas et al. |
| 9,955,981 B2 | 5/2018 | Kulas et al. |
| 10,265,082 B2 | 4/2019 | Vu et al. |
| 10,335,166 B2 | 7/2019 | Kulas et al. |
| 10,507,028 B2 | 12/2019 | Kulas et al. |
| 10,786,266 B2 | 9/2020 | Kulas et al. |
| 2003/0097133 A1 | 5/2003 | Green et al. |
| 2004/0057803 A1 | 3/2004 | Walrath |
| 2005/0053439 A1 | 3/2005 | Wang et al. |
| 2005/0203526 A1 | 9/2005 | Ellis |
| 2005/0272004 A1 * | 12/2005 | Desrosiers ........... A61C 8/0089 |
| | | 433/102 |
| 2005/0273107 A1 | 12/2005 | Stevens |
| 2005/0283160 A1 | 12/2005 | Knisely et al. |
| 2006/0045639 A1 | 3/2006 | Flynn et al. |
| 2006/0067797 A1 | 3/2006 | Calamia |
| 2006/0085005 A1 | 4/2006 | Kenealy et al. |
| 2006/0129061 A1 | 6/2006 | Kaneto et al. |
| 2006/0142775 A1 | 6/2006 | Heneberry et al. |
| 2006/0269372 A1 | 11/2006 | Goshima |
| 2007/0010822 A1 | 1/2007 | Zalenski et al. |
| 2007/0160437 A1 | 7/2007 | Shultz et al. |
| 2007/0163416 A1 * | 7/2007 | Burgess ................. B23D 61/04 |
| | | 83/855 |
| 2007/0213736 A1 | 9/2007 | Ducharme |
| 2007/0280792 A1 | 12/2007 | Kochan et al. |
| 2007/0298376 A1 | 12/2007 | Kmiecz et al. |
| 2008/0132929 A1 * | 6/2008 | O'Sullivan ........ A61B 17/1615 |
| | | 606/170 |
| 2008/0140078 A1 | 6/2008 | Nelson et al. |
| 2008/0167653 A1 | 7/2008 | Watlington et al. |
| 2008/0177294 A1 | 7/2008 | O'Neil et al. |
| 2008/0193234 A1 | 8/2008 | Davancens et al. |
| 2008/0215148 A1 | 9/2008 | Lesinski et al. |
| 2009/0023988 A1 | 1/2009 | Korner et al. |
| 2009/0024129 A1 | 1/2009 | Gordon et al. |
| 2009/0031871 A1 * | 2/2009 | Malandain ......... A61B 17/3205 |
| | | 83/53 |
| 2009/0048602 A1 | 2/2009 | O'Donoghue |
| 2009/0138015 A1 | 5/2009 | Conner et al. |
| 2009/0216235 A1 * | 8/2009 | Ellis ..................... B23B 51/00 |
| | | 408/199 |
| 2009/0222009 A1 | 9/2009 | Ellis |
| 2009/0264888 A1 | 10/2009 | Neumeyer et al. |
| 2010/0054884 A1 | 3/2010 | Masuda et al. |
| 2010/0057087 A1 | 3/2010 | Cha |
| 2010/0121365 A1 * | 5/2010 | O'Sullivan ........ A61B 17/1615 |
| | | 606/170 |
| 2010/0145341 A1 | 6/2010 | Ranck et al. |
| 2010/0178631 A1 | 7/2010 | Gordils Wallis et al. |
| 2010/0209200 A1 | 8/2010 | Delacretaz |
| 2010/0286695 A1 | 11/2010 | Hannani et al. |
| 2011/0015634 A1 | 1/2011 | Smith et al. |
| 2011/0054884 A1 | 3/2011 | Drakwall et al. |
| 2011/0098710 A1 | 4/2011 | Spratt et al. |
| 2011/0112540 A1 | 5/2011 | McLean et al. |
| 2011/0208194 A1 | 8/2011 | Steiner et al. |
| 2011/0211922 A1 | 9/2011 | Maeda et al. |
| 2011/0238070 A1 | 9/2011 | Santangelo et al. |
| 2011/0238099 A1 | 9/2011 | Loreth |
| 2012/0041564 A1 * | 2/2012 | Landon ............... A61F 2/30767 |
| | | 623/20.34 |
| 2012/0063860 A1 | 3/2012 | Wada et al. |
| 2012/0150209 A1 * | 6/2012 | Gubellini ........... A61B 17/1615 |
| | | 606/170 |
| 2012/0158028 A1 * | 6/2012 | O'Sullivan ...... A61B 17/32002 |
| | | 606/170 |
| 2012/0330315 A1 | 12/2012 | Ranck et al. |
| 2013/0028677 A1 | 1/2013 | Schwaegert et al. |
| 2013/0051937 A1 | 2/2013 | Volokh et al. |
| 2013/0166034 A1 * | 6/2013 | Landon ............... A61B 17/1659 |
| | | 623/20.2 |
| 2013/0274779 A1 * | 10/2013 | Kulas ................ A61B 17/1615 |
| | | 606/180 |
| 2014/0058423 A1 | 2/2014 | Smith et al. |

(56) References Cited

U.S. PATENT DOCUMENTS

| | | | | |
|---|---|---|---|---|
| 2015/0025559 A1* | 1/2015 | Kulas | ............... | A61B 17/1615 606/180 |
| 2015/0173776 A1* | 6/2015 | Burke | ............... | A61B 17/1613 606/80 |
| 2015/0297243 A1* | 10/2015 | Kulas | ............... | A61B 17/1695 606/80 |
| 2016/0287267 A1 | 10/2016 | Kulas et al. | | |
| 2017/0056026 A1 | 3/2017 | Vu et al. | | |
| 2018/0153562 A1 | 6/2018 | Kulas et al. | | |
| 2018/0206855 A1 | 7/2018 | Kulas et al. | | |
| 2018/0242986 A1 | 8/2018 | Kulas et al. | | |
| 2019/0239898 A1 | 8/2019 | Vu et al. | | |

FOREIGN PATENT DOCUMENTS

| | | | |
|---|---|---|---|
| CN | 204562293 U | 8/2015 | |
| DE | 19826276 C1 | 11/1999 | |
| DE | 102010010589 A1 | 9/2011 | |
| EP | 0332437 A3 | 8/1990 | |
| EP | 1872739 A1 | 1/2008 | |
| EP | 2561822 A2 | 2/2013 | |
| EP | 3698731 A1 | 8/2020 | |
| GB | 2452158 A | 2/2009 | |
| JP | H06155126 A | 6/1994 | |
| JP | H07108409 A | 4/1995 | |
| JP | 10-263914 | 10/1998 | |
| JP | H10-263914 A | 10/1998 | |
| JP | 2003291024 A | 10/2003 | |
| JP | 2005125465 A | 5/2005 | |
| JP | 2006512214 A | 4/2006 | |
| JP | 2006523542 A | 10/2006 | |
| JP | 2008501541 A | 1/2008 | |
| JP | 2009501597 A | 1/2009 | |
| JP | 200923055 A | 2/2009 | |
| JP | 2010-510042 A | 4/2010 | |
| JP | 2013502943 A | 1/2013 | |
| JP | 2013527781 A | 7/2013 | |
| JP | 2013166232 A | 8/2013 | |
| JP | 2014012302 A | 1/2014 | |
| JP | 2014-121194 A | 6/2014 | |
| WO | 2006/026482 A2 | 3/2006 | |
| WO | 2007010389 A1 | 1/2007 | |
| WO | 2008061711 A2 | 5/2008 | |
| WO | 2008064350 A2 | 5/2008 | |
| WO | 2009063261 A1 | 5/2009 | |
| WO | 2010061933 A1 | 6/2010 | |
| WO | 2011023381 A1 | 3/2011 | |
| WO | 2011132876 A2 | 10/2011 | |
| WO | 2012083468 A1 | 6/2012 | |
| WO | 2013056262 A1 | 4/2013 | |
| WO | 2013/151770 A1 | 10/2013 | |
| WO | 2013158469 A1 | 10/2013 | |
| WO | 2014037518 A1 | 3/2014 | |
| WO | WO-2014037518 A1 * | 3/2014 | ............ A61B 17/16 |
| WO | 2015009810 A1 | 1/2015 | |
| WO | 2015160884 A1 | 10/2015 | |

OTHER PUBLICATIONS

Office Action mailed Sep. 28, 2020 in corresponding/related Japanese Application No. 2018-530653.
Office Action mailed Dec. 10, 2021, in corresponding/related European Application No. 16714680.2.
Second Office Action regarding Chinese Patent Application No. 201680057692.0, dated Jan. 21, 2021.
Canadian Office Action regarding Canadian Application No. 3,076,639, mailed Apr. 13, 2021.
Office Action regarding Japanese Patent Application No. 2020-037614 (with English Translation), dated May 10, 2021.
Japanese Office Action issued in corresponding Japanese Application No. 2021-130485 dated Jul. 29, 2022, 4 pages.
Office Action regarding Japanese Patent Application No. 2018-530653, dated May 13, 2021.
Examination Report regarding Indian Patent Application No. 20183700762.8, dated Jul. 12, 2021.
Australian Office Action dated Jun. 23, 2015 for AU Application No. 2013249626, for PCT/US2013/036269 which claims benefit of U.S. Appl. No. 13/447,372, filed Apr. 16, 2012.
Australian Office Action mailed Apr. 12, 2018 in corresponding/related Australian Application No. 2014290106.
Australian Office Action mailed Mar. 15, 2017 for AU Application No. 2015247768.
Australian Office Action mailed Mar. 21, 2018 in corresponding/related Australian Application No. 2016234968.
Canadian Office Action dated Sep. 29, 2015 for Canadian Application No. 2,870,689 claiming benefit of PCT/US2013/036269.
Canadian Office Action dated Aug. 4, 2016 for CA Application No. 2870689 for PCT/US2013/036269 which claims benefit of U.S. Appl. No. 13/447,372, filed Apr. 16, 2012.
Canadian Office Action mailed Aug. 22, 2017 in corresponding/related Canadian Application No. 2,945,806.
Canadian Office Action mailed Feb. 2, 2018 in corresponding/related Canadian Application No. 2,917,601.
Canadian Office Action mailed Jun. 7, 2018 in corresponding/related Canadian Application No. 2,945,806.
Canadian Office Action mailed May 1, 2017 for CA Application No. 2,917,601.
Canadian Office Action mailed Sep. 29, 2015 for Canadian Application 2,870,689 claiming benefit of International Application PCT/US2013/036269 claiming benefit of U.S. Appl. No. 13/447,372, filed Apr. 16, 2012.
Chinese Office Action (English translation) dated May 24, 2016 for Chinese Application No. 2013800311659 which claims benefit of PCT/2013/036269 filed Apr. 12, 2013.
Chinese Office Action mailed Nov. 6, 2018 in corresponding/related Chinese Application No. 201710146560.1.
End Mill and Cutting Tool Design Criteria and Technical Features. Melin Tool Company. Retrieved from <http://www.endmill.com/pages/training/design.html on Jun. 14>, 2013. (pp. 1-4).
European Office Action dated Dec. 15, 2015 for EP Application No. 13720176.0-1654.
European Office Action dated Dec. 15, 2015 for European Application No. 13720176.0-1654 claiming benefit of PCT/US2013/036269.
European Office Action mailed Jul. 27, 2017 in corresponding European Application No. 14747254.2.
Examination Report mailed Jul. 15, 2020 in corresponding/related Australian Application No. 2016315693.
Examination Report mailed Jun. 30, 2020 in corresponding/related Australian Application No. 2019204541.
Examination Report mailed May 26, 2020 in corresponding/related Australian Application No. 2019206060.
Extended European Search Report mailed Jul. 22, 2020 in corresponding/related European Application No. 20169211.8.
Extended European Search Report mailed Jul. 3, 2017 in corresponding European Application No. 17151461.5.
Find Your Perfect Balance. Midas Rex Legend 7.5. cm Attachments and Tools. Medtronic brochure. (2012) 3 pages.
Innovations 2005 catalog, Komet Gebr. Brasseler GmbH & Co., KG, Lemgo, Germany, 28 pages.
International Preliminary Report on Patentability and Written Opinion mailed Jan. 19, 2016 for PCT/US2014/046827, claiming priority to U.S. Appl. No. 13/944,650, filed Jul. 17, 2013.
International Preliminary Report on Patentability and Written Opinion mailed Jan. 28, 2016 for PCT/US2014/046827 which claims benefit of U.S. Appl. No. 13/944,650, filed Jul. 17, 2013.
International Preliminary Report on Patentability and Written Opinion mailed Oct. 30, 2014 for PCT/US2013/036269, claiming priority to U.S. Appl. No. 13/447,372, filed Apr. 16, 2012.
International Preliminary Report on Patentability dated Oct. 27, 2016 for Application No. PCT/US2015/025867 filed Apr. 15, 2015.
International Preliminary Report on Patentability mailed Mar. 15, 2018 in corresponding/related International Application No. PCT/US2016/049464.

(56) References Cited

OTHER PUBLICATIONS

International Preliminary Report on Patentability mailed Oct. 12, 2017 in corresponding International Application No. PCT/US2016/023349.
International Search Report and Written Opinion dated Jan. 3, 2017 for PCT/US2016/049464 claiming benefit of U.S. Appl. No. 14/840,217, filed Aug. 31, 2015.
International Search Report and Written Opinion dated Jul. 25, 2016 for PCT/US2016/023349 which claims benefit the benefit of U.S. Appl. No. 14/674,002 fild Mar. 31, 2015.
International Search Report and Written Opinion mailed Aug. 28, 2013 for PCT/US2013/036269, claiming priority to U.S. Appl. No. 13/447,372, filed Apr. 16, 2012.
International Search Report and Written Opinion mailed Jan. 19, 2016 for Application No. PCT/US2014/046827 which claims benefit of U.S. Appl. No. 13/944,650, filed Jul. 17, 2013.
International Search Report and Written Opinion mailed Jan. 28, 2016 for Application No. PCT/US2014/046827 which claims benefit of U.S. Appl. No. 13/944,650, filed Jul. 17, 2013.
International Search Report and Written Opinion mailed Jul. 25, 2016 for Application No. PCT/US2014/046827 which claims benefit of U.S. Appl. No. 13/944,650, filed Jul. 17, 2013.
International Search Report and Written Opinion mailed Oct. 10, 2014 for PCT/US2014/046827 claiming benefit of U.S. Appl. No. 13/944,650, filed Jul. 17, 2013.
International Search Report and Written Opinion mailed Oct. 22, 2015 corresponding to PCT/US2015/025867 filed Apr. 15, 2015.
Japanese Office Action corresponding to Japanese Application No. 2016-562744 mailed Sep. 4, 2019.
Japanese Office Action mailed Nov. 10, 2015 for Japanese Application 2015-507064 claiming benefit of PCT/US2014/046827 claiming benefit of U.S. Appl. No. 13/944,650, filed Jul. 17, 2013.
Japanese Office Action mailed Nov. 10, 2015 for Japanese Application No. 2015-507064 claiming benefit of PCT/US2014/046827 claiming benefit of U.S. Appl. No. 13/944,650, filed Jul. 17, 2013.
Japanese Office Action mailed Apr. 19, 2018 in corresponding/related Japanese Application No. 2016-527065.
Japanese Office Action mailed Jun. 21, 2016 for Japanese Application No. 2015-50764 claiming benefit of PCT/US2013/036269 claiming benefit of U.S. Appl. No. 13/447,372, filed Apr. 12, 2013 with English translation.
Komet Burs mini catalogue 2007, Henry Schein Halas, www.henryschein.com.au, 19 pages.
Komet Surgery catalog, Mar. 2011, 8 pages.
Korean Office Action dated Mar. 16, 2016 for KR Application No. 10-2014-7031869 for PCT/US2013/036269 which claims benefit of U.S. Appl. No. 13/447,372, filed Apr. 16, 2012 with English translation.
Korean Office Action for corresponding/related KR Patent Application No. 10-2014-7031869 dated Mar. 16, 2016.
Korean Office Action mailed Dec. 7, 2018 in corresponding/related Chinese Application No. 10-2017-7031086.
Korean Office Action mailed Feb. 19, 2018 in corresponding/related Korean Application No. 10-2016-7031697.
Canadian Office Action issued in corresponding Canadian Application No. 2,981,264 dated Sep. 2, 2022, 6 pages.
Korean Office Action mailed Jul. 12, 2018 in corresponding/related Korean Application No. 10-2016-7031697.
Korean Office Action mailed Sep. 30, 2016 for Korean Application No. 10-2014-7031869 corresponding to PCT/US2013/036269 which claims benefit of U.S. Appl. No. 13/447,372, filed Apr. 16, 2012 with English translation.
Office Action mailed Dec. 3, 2019 in corresponding/related Canadian Application No. 2945806.
Office Action mailed Jan. 7, 2019 in corresponding/related European Application No. 18191962.2.
Office Action mailed Mar. 1, 2019 in corresponding Canadian Application No. 2,945,806.
Office Action mailed Mar. 26, 2019 in corresponding/related Japanese Application No. 2016-562744.
Office Action mailed May 7, 2020 in corresponding/related Chinese Application No. 201680057692.0.
Office Action mailed Nov. 21, 2019 in corresponding/related Australian Application No. 2016244068.
Office Action mailed Nov. 28, 2019 in corresponding/related Chinese Application No. 201680031174.1.
Office Action mailed Nov. 29, 2019 in corresponding/related Indian Application No. 2053/MUMNP/2014.
Office Action mailed Oct. 24, 2019 in corresponding/related European Application No. 16763164.7.
Office Action regarding corresponding/related Brazilian Patent Application No. 112014025681.0, dated Jan. 21, 2020.
Office Action regarding corresponding/related Japanese Patent Application No. 2017550635, dated Jan. 29, 2020.
Stryker Neuro Spine ENT brochure, Zyphr Burs, Kalamazoo, Michigan, www.stryker.com, 2011, 6 pages.
Table of Contents, RedLine Tools catalog, www.redlinetools.com/Images/PDFs/Redline09/RL062009_Sec1_Front%20pl-9_72.pdf, pp. 1-8.
U.S. Appl. No. 14/674,002, U.S. Pat. No. 9,955,981, filed Mar. 31, 2015, Kulas, et al.
U.S. Appl. No. 15/966,778, U.S. Pat. No. 10,786,266, filed Apr. 30, 2018, Kulas, et al.
U.S. Appl. No. 15/886,260, 2018-0153562, filed Feb. 1, 2018, Kulas, et al.
U.S. Appl. No. 16/390,476, 2019-0239898, filed Aug. 8, 2019, Kulas, et al.
U.S. Appl. No. 16/458,923, 2019-0321053, filed Jul. 1, 2019, Kulas, et al.
U.S. Appl. No. 16/716,019, 2020-0113582, filed Dec. 16, 2019, Kulas, et al.
European Office Action regarding Patent Application No. 20169211.8, dated Mar. 9, 2022.
Office Action regarding Korean Patent Application No. 10-2016-7003354 (with English Translation), dated Apr. 2, 2021.
Third Office Action regarding corresponding Chinese Application No. 201680031174.1 (With English Translation), mailed May 6, 2021.
Examination Report regarding Australian Patent Application No. 2020244386, dated May 28, 2021.

\* cited by examiner

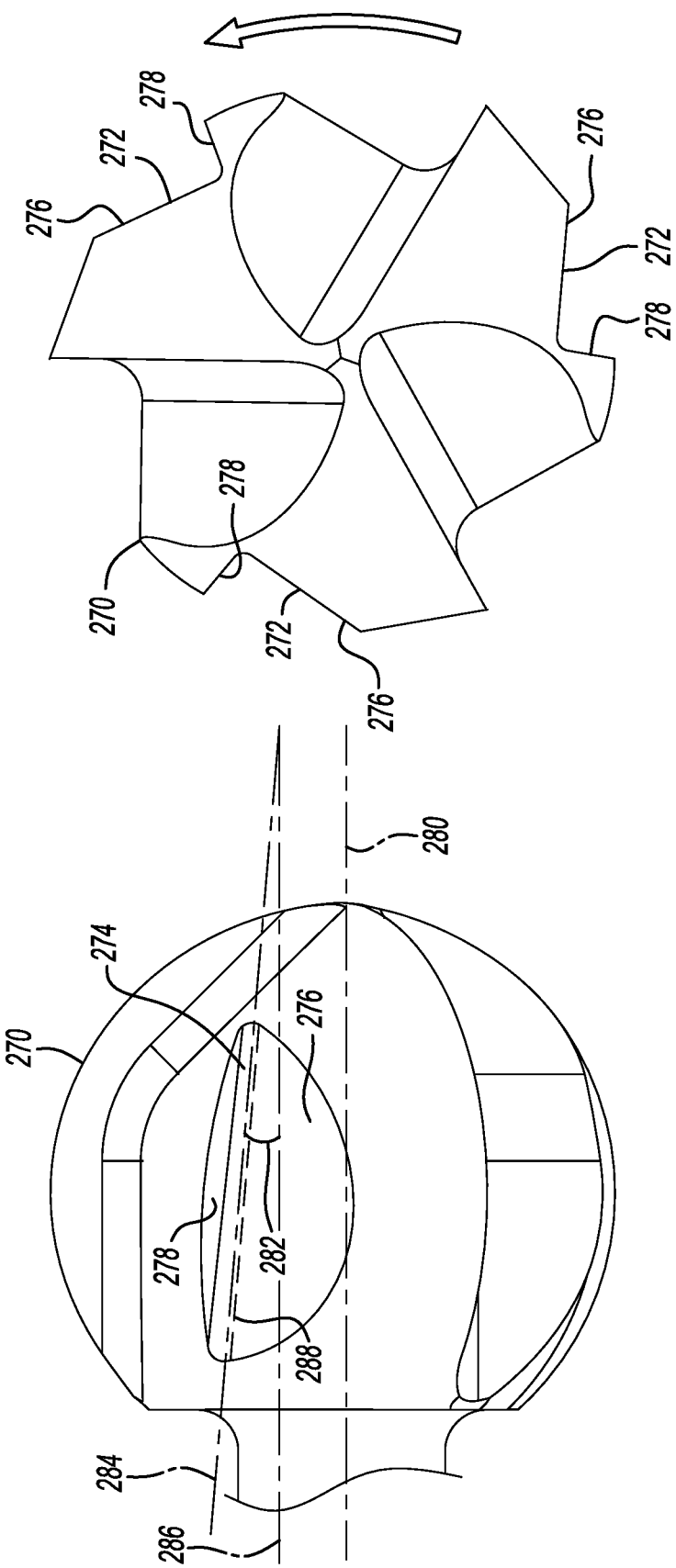

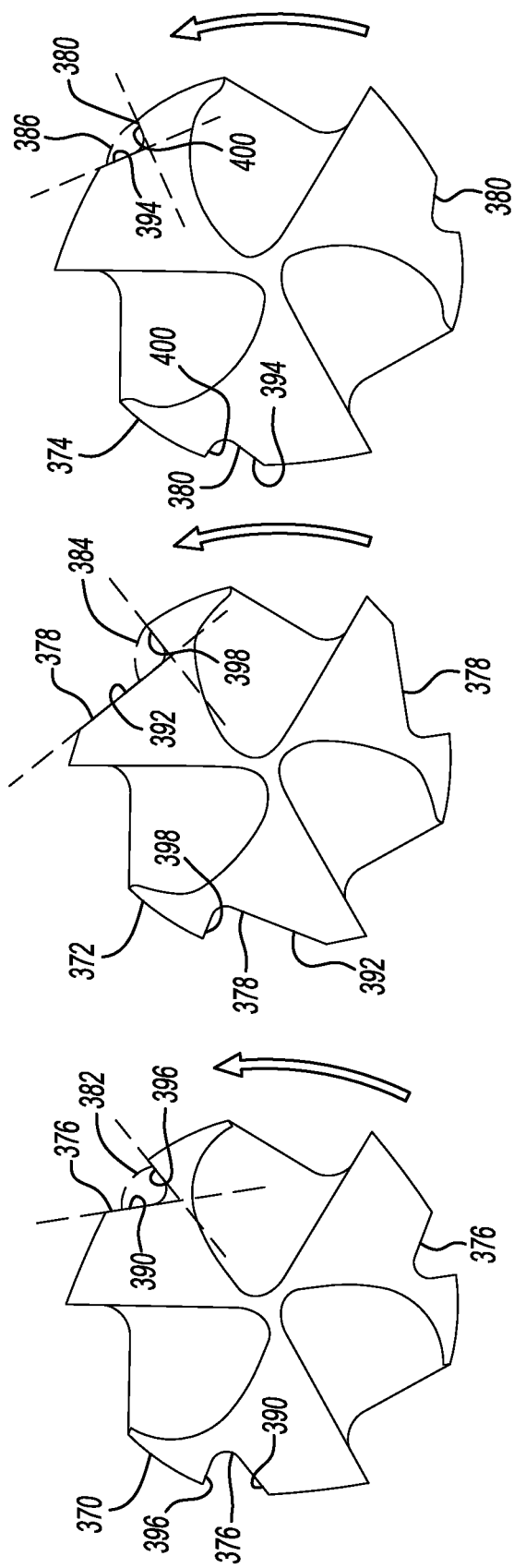

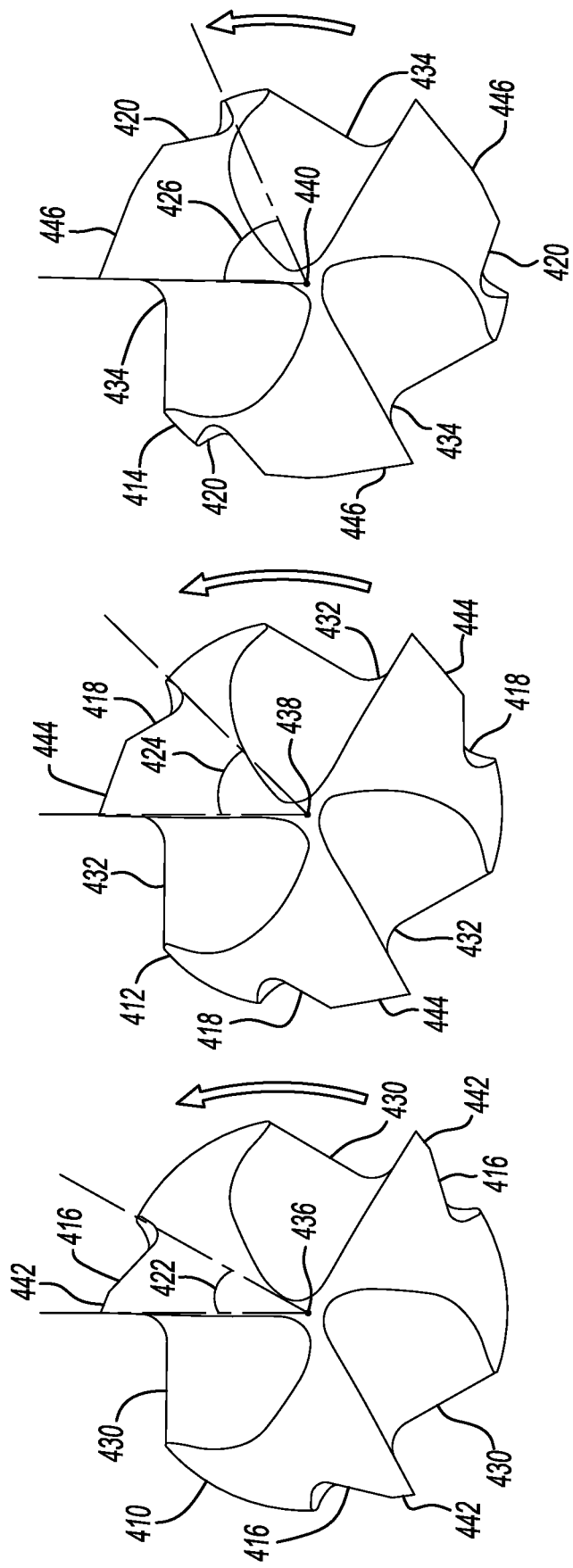

SURGICAL BURS WITH LOCALIZED AUXILIARY FLUTES

CROSS-REFERENCE TO RELATED APPLICATIONS

The application is a continuation of U.S. patent application Ser. No. 15/966,778 filed on Apr. 30, 2018, which is a continuation of U.S. patent application Ser. No. 14/674,002 filed on Mar. 31, 2015, now U.S. Pat. No. 9,955,981 issued on May 1, 2018. The entire disclosures of the above applications are incorporated herein by reference.

FIELD

The disclosure relates to a surgical systems for bone cutting or shaping, and more particularly to surgical burs.

BACKGROUND

This section provides background information related to the present disclosure which is not necessarily prior art.

A surgical instrument may include a motor housing with a grip, an attachment, and a surgical tool. The attachment and the surgical tool may be replaced with other attachments and surgical tools. The attachment may connect to the motor housing and engage with a motor in the motor housing. The surgical tool may include a shaft and a surgical bur. The shaft extends from the surgical bur, engages with the attachment and is axially rotated by the motor.

Surgical burs are used to dissect, cut and/or shape bone during a surgical procedure. Surgical burs have various characteristics that can often conflict with each other. Some of these characteristics include cutting efficiency, stability, working length, and visibility. Improving one of these characteristics can negatively affect one or more of the other characteristics. As an example, when an enhancement is provided in an axial region (or at a tip of the surgical bur) or in a radial region (or at an equator of a surgical bur), cutting performance in other regions of the surgical bur can be negatively affected.

A length of a shaft of a surgical tool affects a working length of the surgical instrument. The working length refers to a length of the surgical instrument from a grip (or motor housing) to a cutting portion of a corresponding surgical bur. The working length includes an attachment length and an exposed length. The attachment length refers to a length of a corresponding attachment. The attachment is a portion of a surgical instrument extending from a motor (or main) housing to an exposed portion of a shaft of a surgical tool. The exposure length refers to a length of a surgical tool that is exposed subsequent to being engaged with an attachment of a surgical instrument. The exposure length is a length of a portion of the surgical tool extending from a distal end of the attachment. A distal end of a surgical bur can come in contact with tissue of a patient. The term "distal" means furthest away from a medical practitioner holding a surgical instrument with a surgical bur. The term "proximal" means towards the medical practitioner and away from the patient.

A surgeon may desire increased exposure without changing a length of a surgical tool (or working length). This may be provided by using a surgical tool with a shorter attachment and/or providing a variable exposure attachment. A variable exposure attachment allows a surgeon to change an amount of a shaft of a surgical tool that extends from the variable exposure attachment. Increasing the exposure tends to increase instability of the surgical tool. The longer the shaft of the surgical bur that extends away from the attachment, the more unstable the surgical bur can be during axial rotation of the surgical bur.

SUMMARY

This section provides a general summary of the disclosure, and is not a comprehensive disclosure of its full scope or all of its features.

A surgical bur is provided and includes primary flutes and auxiliary flutes. The primary flutes include (i) first clearance surfaces, and (ii) first rake surfaces with first cutting edges. The primary flutes extend from a proximal end of the surgical bur to a distal end of the surgical bur. The auxiliary flutes are localized in distal, central, and/or proximal regions of the surgical bur. The auxiliary flutes include (i) second clearance surfaces, and (ii) second rake surfaces with second cutting edges. At least one of the auxiliary flutes is located between a pair of adjacent ones of the primary flutes.

In other features, a surgical bur is provided and includes an equator, primary flutes, and auxiliary flutes. The primary flutes include (i) first clearance surfaces, and (ii) first rake surfaces with first cutting edges. The auxiliary flutes include (i) second clearance surfaces, and (ii) second rake surfaces with second cutting edges. At least one of the auxiliary flutes is located between a pair of adjacent ones of the primary flutes and does not extend across the equator of the surgical bur.

In other features, a surgical bur is provided and includes primary flutes and auxiliary flutes. The primary flutes include (i) first clearance surfaces, and (ii) first rake surfaces with first cutting edges. At least one of the primary flutes extends from a proximal end of the surgical bur to a distal end of the surgical bur. The auxiliary flutes include (i) second clearance surfaces, and (ii) second rake surfaces with second cutting edges. Each of the auxiliary flutes is located between a pair of adjacent ones of the primary flutes. At least one of the auxiliary flutes does not extend to the distal end of the surgical bur.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 15 is a radial side view of a ball style surgical bur illustrating auxiliary flutes with a right-hand flute axial angle in accordance with the present disclosure.

FIG. 16 is a distal end view of the ball style surgical bur of FIG. 15.

FIG. 24 is a distal end view of a ball style surgical bur illustrating auxiliary flutes with a first inside flute angle in accordance with the present disclosure.

FIG. 25 is a distal end view of a ball style surgical bur illustrating auxiliary flutes with a second inside flute angle in accordance with the present disclosure.

FIG. 26 is a distal end view of a ball style surgical bur illustrating shallow auxiliary flutes with the second inside flute angle and a particular radial rake angle in accordance with the present disclosure.

FIG. 27 is a distal end view of a ball style surgical bur illustrating auxiliary flutes with a first clock angle in accordance with the present disclosure.

FIG. 28 is a distal end view of a ball style surgical bur illustrating auxiliary flutes with a second clock angle in accordance with the present disclosure.

FIG. 29 is a distal end view of a ball style surgical bur illustrating auxiliary flutes with a third clock angle in accordance with the present disclosure.

Corresponding reference numerals indicate corresponding parts throughout the several views of the drawings.

DETAILED DESCRIPTION

Figure 1:
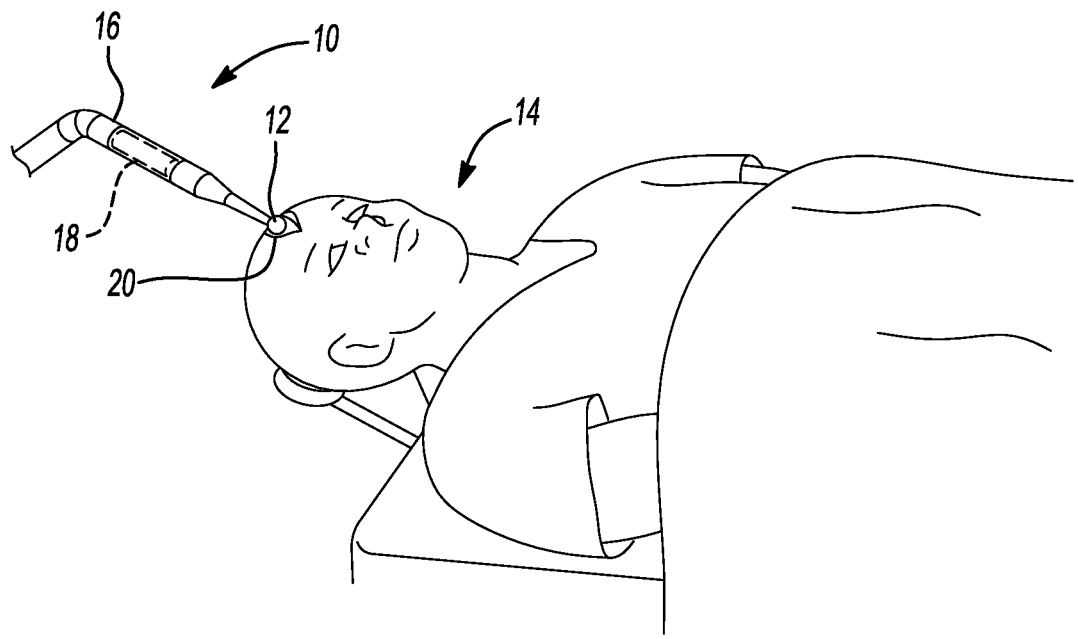
FIG. 1 is a perspective view of a surgical instrument incorporating a surgical bur in accordance with an embodiment of the present disclosure.

Example embodiments will now be described more fully with reference to the accompanying drawings. The following description is merely exemplary in nature and is not intended to limit the present disclosure, application, or uses. It should be understood that throughout the drawings, corresponding reference numerals indicate like or corresponding parts and features.

The following examples include localized flute features for improving multiple characteristics of surgical burs. The term "localized" as used herein refers to one or more features and/or characteristics of a surgical bur that are located in and/or provided by certain regions of the surgical bur and not located in or provided by other regions of the surgical bur. The localized flute features improve one or more characteristics in respective regions of the surgical burs without negatively affecting one or more characteristics of the surgical burs in other regions of the surgical burs. The localized flute features can augment cutting features of the surgical burs, provide stability, and/or improve cutting efficiency.

FIG. 1 shows a surgical instrument 10 incorporating a rotating surgical bur 12, which is being used on a patient 14. For example only, the patient 14 may be undergoing a neurological operation, as shown. FIG. 1 is provided for example purposes only. The surgical burs disclosed herein may be used in different tools and/or cutter assemblies and may be used for other procedures and/or operations. The surgical instrument 10 includes a tool driver 16 that has a motor 18 for axially rotating the surgical bur 12. As shown, the surgical bur 12 may be used to dissect and/or shape a portion of bone and adjacent tissue of the patient 14 in a surgical access site 20.

Figure 2:
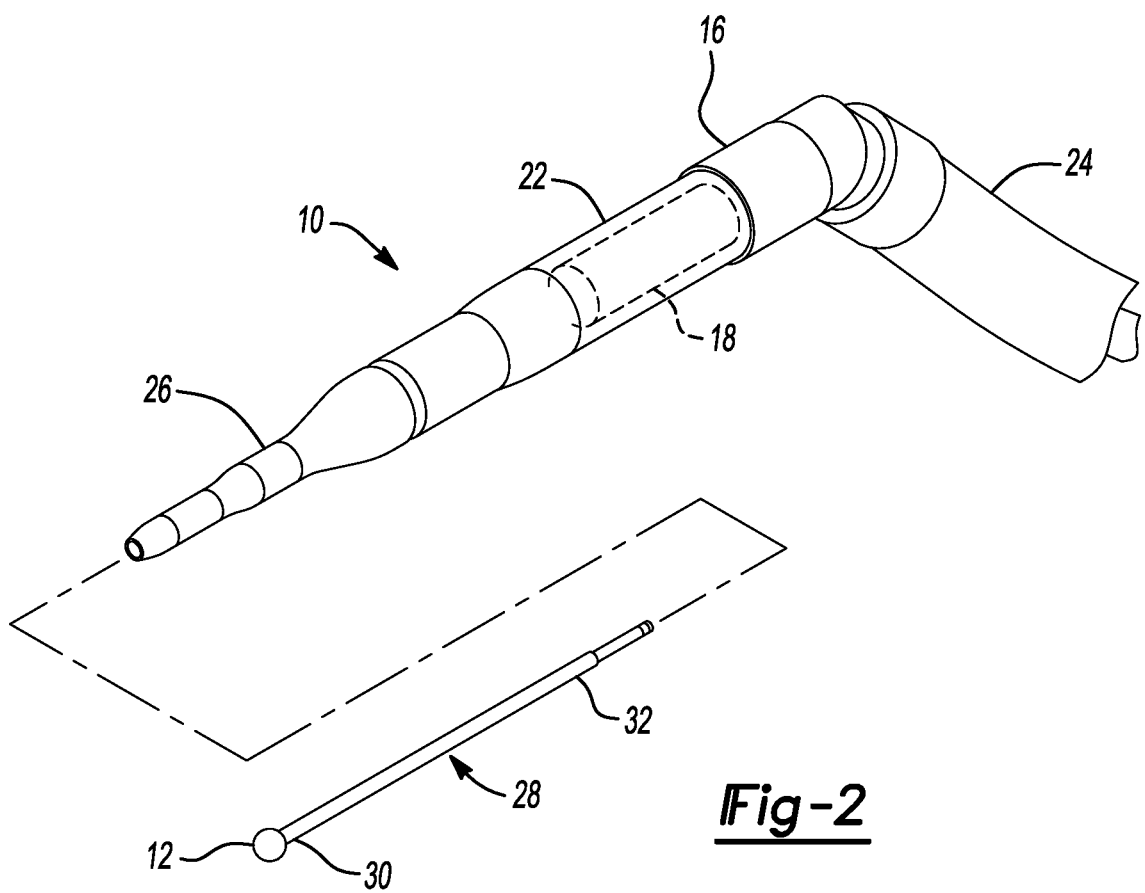
FIG. 2 is a perspective view of the surgical instrument of FIG. 1.

FIG. 2 is a perspective view of the surgical instrument 10. The tool driver 16 includes a motor housing 22 connected to a hose or cable assembly 24. The hose assembly 24 supplies external power and/or pneumatic pressure for the motor 18. The tool driver 16 further includes an attachment 26 that connects to the motor housing 22 and engages with a surgical tool 28. A distal end 30 of the surgical tool 28 includes the surgical bur 12 that is attached to a shaft 32, which engages with the attachment 26. Examples of surgical tools that may be used in replacement of the surgical tool 28 are shown and described below with reference to FIGS. 3-21.

In the following sections various surgical tools and surgical burs are disclosed. Although each of the surgical tools are described as having certain features such as certain angles, depths, etc., the features of each one of the surgical burs may be implemented on any other one of the surgical burs.

Figure 3:
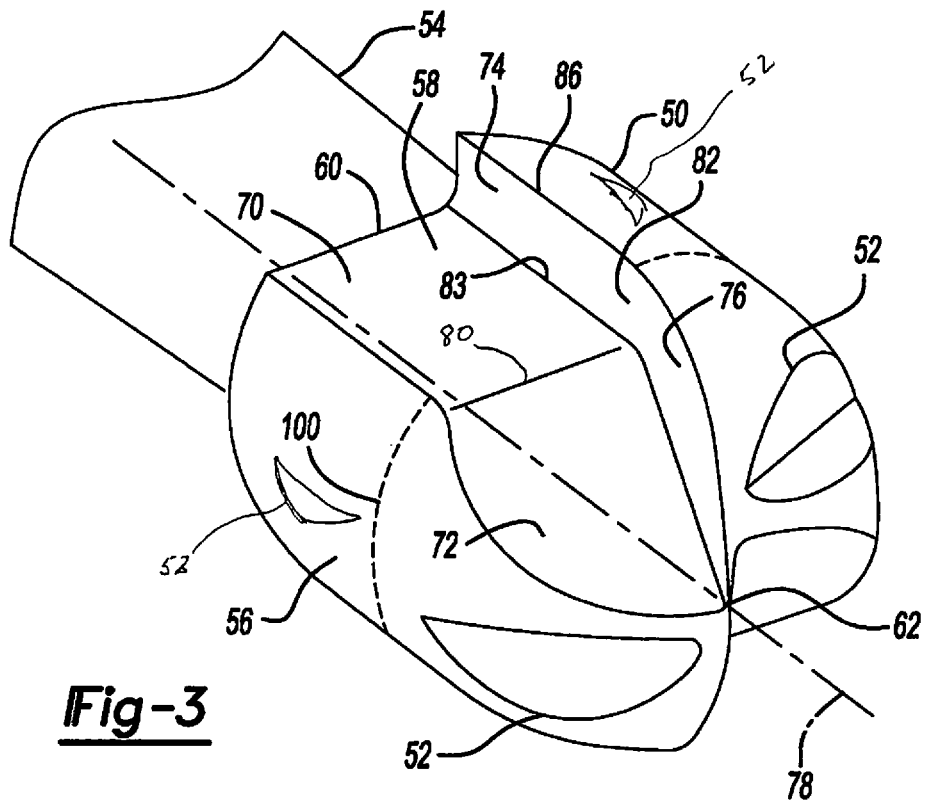
FIG. 3 is a perspective view of a match head (or 'neuro') style surgical bur incorporating auxiliary flutes in a distal region in accordance with the present disclosure.
Figure 4:
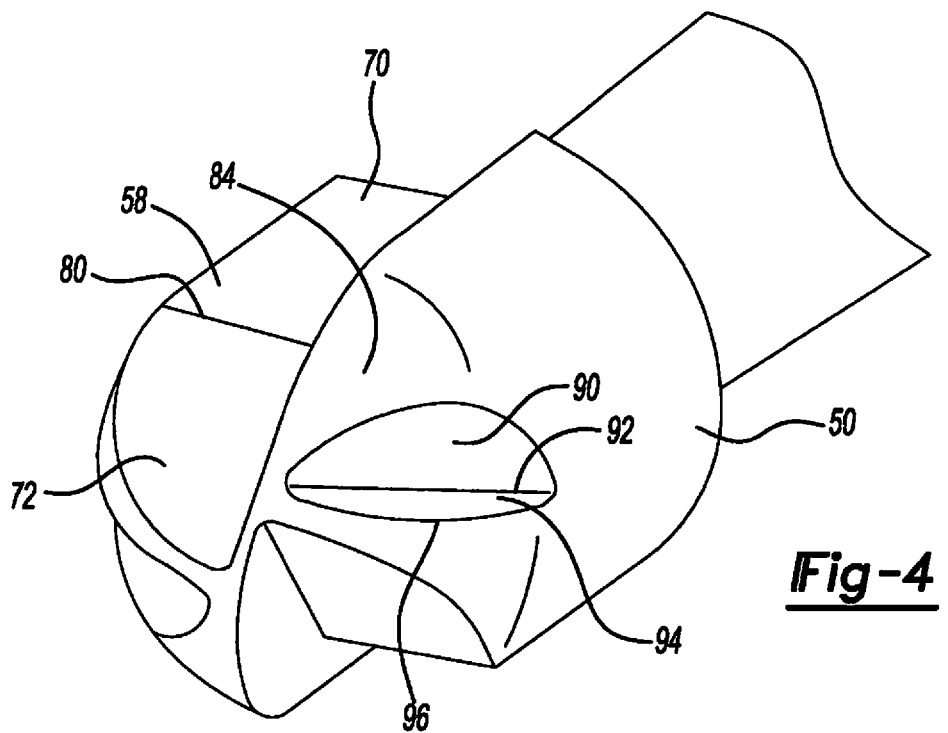
FIG. 4 is another perspective view of the match head style surgical bur of FIG. 3.
Figure 5:
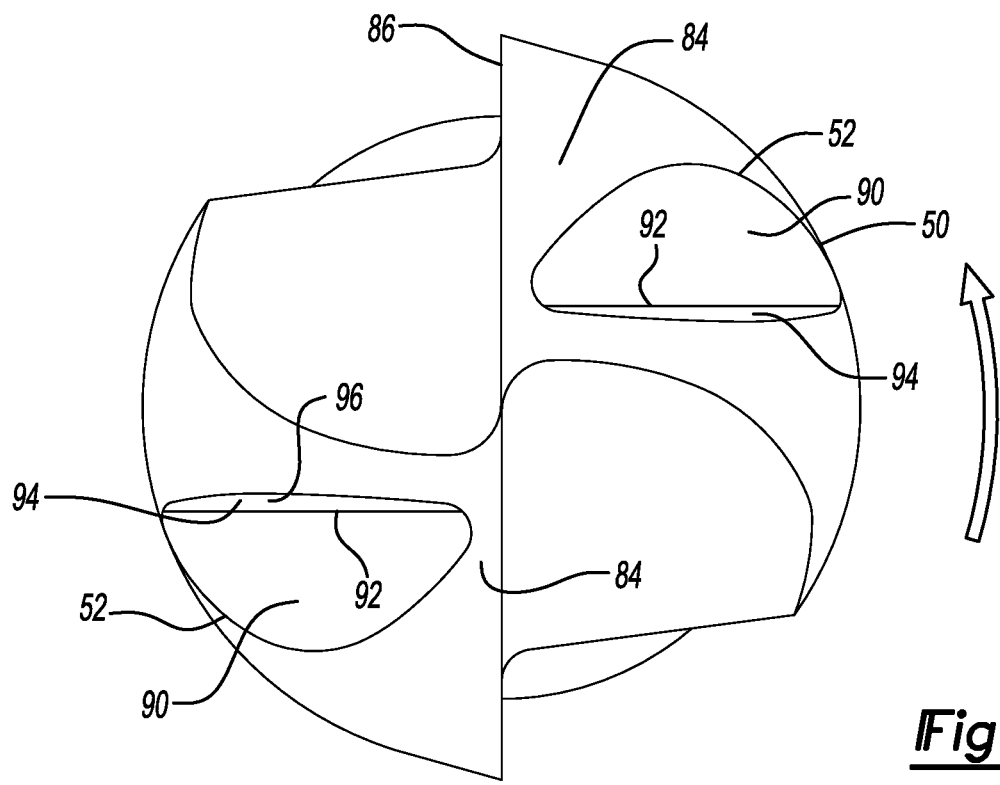
FIG. 5 is a distal end view of the match head style surgical bur of FIG. 3.

FIGS. 3-5 show a surgical bur 50 incorporating discrete auxiliary flutes 52. The surgical bur 50 is a match head (or 'neuro') style surgical bur and extends from a tapered shaft 54. The shaft 54 may have a smaller diameter at the surgical bur 50 than at a proximal portion of the shaft 54, which engages with an attachment (e.g. attachment 26 of FIG. 2). The surgical bur 50 includes a body 56 with primary (or main) flutes 58 and the auxiliary flutes 52. The main flutes 58 extend a full length of the surgical bur 50 from a proximal end 60 to a distal end (or tip) 62 of the surgical bur 50. The main flutes 58 provide more aggressive cutting (cut away more material per revolution of the surgical bur) than the auxiliary flutes 52. The auxiliary flutes 52 are included to provide localized features, such as localized stability and/or localized increased cutting efficiency. These features may be localized to distal, central, and/or proximal regions of the surgical bur 50. These features can be provided in one region without negatively affecting another region of the surgical bur 50.

Each of the main flutes 58 includes a proximal clearance surface 70, a distal clearance surface 72, a proximal rake surface 74 and a distal rake surface 76. The clearance surfaces 70, 72 and the rake surfaces 74, 76 may be planar surfaces. The proximal clearance surfaces 70 when viewed radially may have positive, neutral or negative taper angles relative to an axis-of-rotation 78 of the surgical bur 50. The distal clearance surfaces 72 when viewed radially may have positive taper angles relative to an axis-of-rotation of the surgical bur 50. Taper angles of the shown distal clearance surfaces 72 are more positive than taper angles of the proximal clearance surfaces 70.

First transition regions 80 exist respectively between the proximal clearance surfaces 70 and the distal clearance surfaces 72. The first transition regions 80 may be convex-shaped regions. Second transition regions 82 exist respectively between the proximal rake surfaces 74 and the distal rake surfaces 76. Each of the main flutes 58 includes a third transition region 83 that exists between (i) one of the proximal clearance surfaces 70 and one of the distal clearance surfaces 72 and (ii) one of the proximal rake surfaces 74 and one of the distal rake surfaces 76. The third transition regions 83 may be concave-shaped regions and extend from the distal end 62 to the proximal end 60.

Each proximal rake surface and distal rake surface pair has a cutting edge 86 that extends along an outer perimeter of the surgical bur 50 from the proximal end 60 to the distal end 62. Primary (or first) relief surfaces 84 exist (i) between the main flutes 58 and the auxiliary flutes 52, and (ii) between the cutting edges 86 of the main flutes 58 and the auxiliary flutes 52.

The auxiliary flutes 52 include clearance surfaces 90, transition regions 92, and rake surfaces 94. The clearance surfaces 90 and the rake surfaces 94 may be planar surfaces and/or may be semi-circular shaped. The clearance surfaces 90 may be referred to as secondary relief surfaces for the main flutes 58. The transition regions 92 are concave-shaped regions between the clearance surfaces 90 and the rake surfaces 94. The rake surfaces 94 include respective cutting edges 96.

Although the auxiliary flutes 52 are shown as being located in distal regions of the surgical bur 50, the auxiliary flutes 52 may be centrally located and extend across an equator 100 from the distal regions to proximal regions. The distal regions are distal of the equator 100. The equator 100 may refer to planar portion (or section) of the surgical bur 50 that is perpendicular to the axis-of-rotation 78 (or longitudinal axis) and may be where a diameter of the surgical bur 50 is at a maximum. If the surgical bur 50 has a constant diameter for an extended portion of the surgical bur 50, as in the example shown, the equator 100 may be at the most distal portion of the surgical bur 50, which has the maximum diameter. As another example, the auxiliary flutes 52 may extend from the distal regions to the proximal end 60. As another example, the auxiliary flutes 52 may be in proximal regions of the surgical bur 50. The proximal regions are proximal to the equator 100.

The auxiliary flutes 52 are distinct from the main flutes 58. Although the transition regions 92 of the auxiliary flutes 52 are shown as not extending radially from the axis-of-rotation 78, the transition regions 92 may extend radially from the axis-of-rotation 78 and/or lay in a plane that includes the axis-of-rotation 78. The auxiliary flutes 52 may be considered "cut-out" sections of relief surfaces of the main flutes 58. As shown, each of the auxiliary flutes 52 extends from the distal end 62, centrally between adjacent main flutes, and towards the equator 100 and/or proximal end 60. Adjacent main flutes refer to two main flutes that do not have another main flute between the two main flutes. Similarly, adjacent auxiliary flutes refer to two auxiliary flutes that do not have another auxiliary flute between the two auxiliary flutes. A main flute may be adjacent to an auxiliary flute without any intervening flute between the main flute and the auxiliary flute.

As shown, the auxiliary flutes 52 are localized to the distal regions. The auxiliary flutes 52 provide increased relief angles for the main flutes 58, which decreases drag during use, and as a result increases spinning efficiency at the distal end 62. The additional cutting edges 96 of the auxiliary flutes 52 increase cutting efficiency at the distal end 62.

Although the surgical bur 50 is shown as having two main flutes 58 and two auxiliary flutes 52 evenly distributed around the axis-of-rotation 78, the surgical bur 50 may have any number of main flutes and auxiliary flutes. In addition, although the surgical bur 50 is shown as having a same number of main flutes as auxiliary flutes, the surgical bur 50 may have a different number of auxiliary flutes than main flutes. Further, more than one auxiliary flute may be cut-out of a relief surface of a main flute. For example, a first auxiliary flute may be located in a distal region of a relief surface of a main flute and a second auxiliary flute may be located in a central and/or proximal region of the relief surface. The second auxiliary flute may be distinct from the first auxiliary flute or the auxiliary flute may share a transition region between the first and second auxiliary flutes. The first and second auxiliary flutes may have respective taper angles, flute axial angles, inside angles, clock angles, radial rake angles, axial rake (or helix) angles, and depths. These angles are further defined below.

A single surgical bur may include auxiliary flutes of the same type and style or may include auxiliary flutes of different types and styles. The auxiliary flutes may have different taper angles, flute axial angles, inside angles, clock angles, radial rake angles, axial rake angles, and depths. Different types and styles of auxiliary flutes having different angles and depths are further described and illustrated below with respect to FIGS. 6-29. Although these angles and depths are described below with respect to ball head style surgical burs, the angles and depths apply to the surgical bur of FIGS. 3-5 and/or other surgical burs encompassed by the numerous examples disclosed herein. Also, although specific angles and depths are shown in FIGS. 6-29, other angles and depths may be implemented.

Figure 6:
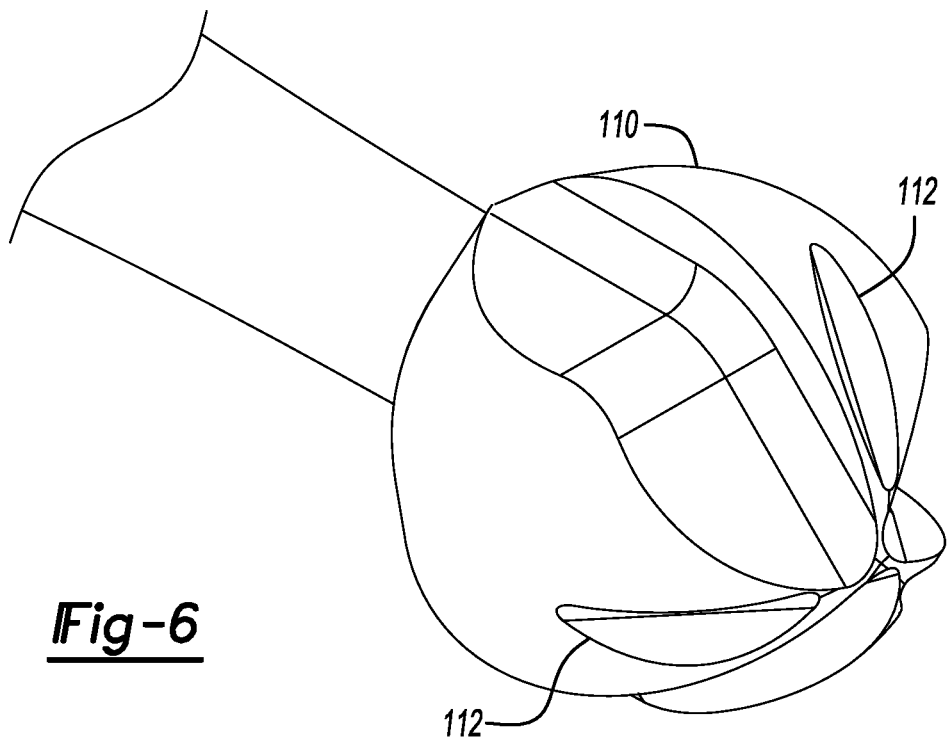
FIG. 6 is a perspective view of a ball head style surgical bur incorporating auxiliary flutes in a distal region in accordance with the present disclosure.

FIG. 6 shows a surgical bur 110 incorporating auxiliary flutes 112. The surgical bur 110 is a ball head style surgical bur. The auxiliary flutes 112 are in distal regions of the surgical bur 110. The auxiliary flutes 112 may be similar to or different than the auxiliary flutes 52 of the surgical bur 50 of FIG. 3-5.

Figure 7:
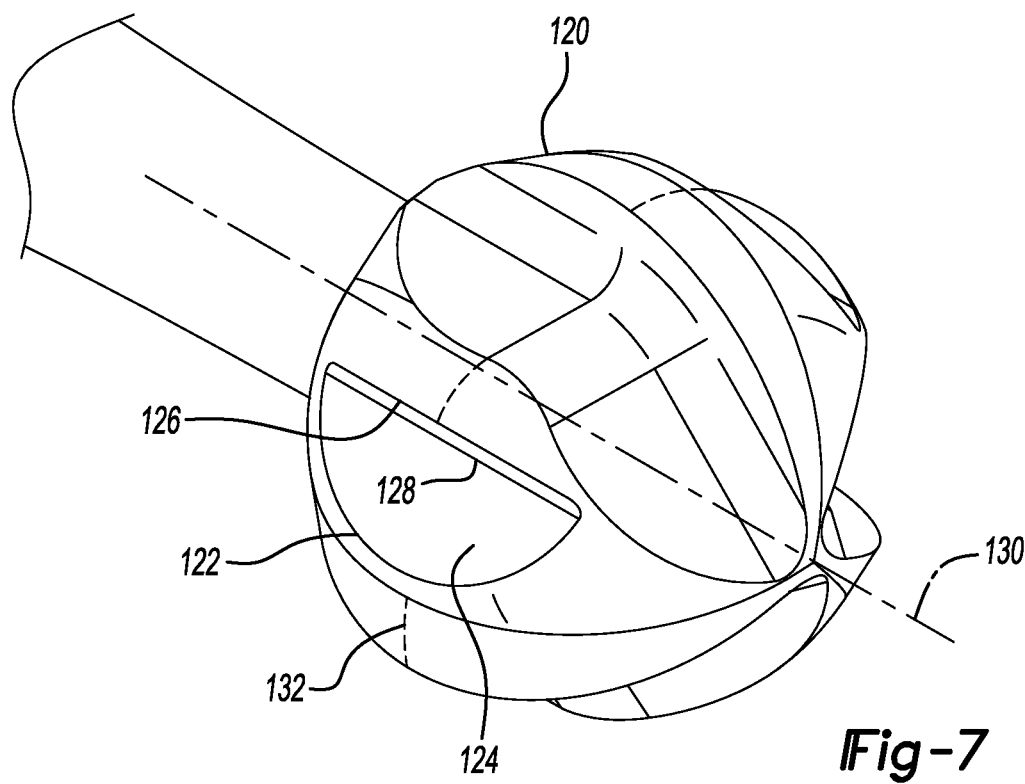
FIG. 7 is a perspective view of another ball head style surgical bur incorporating auxiliary flutes in a central region in accordance with the present disclosure.

FIG. 7 shows a surgical bur 120 incorporating auxiliary flutes 122 (one is visible in FIG. 7). The surgical bur 120 is a ball head style surgical bur. The auxiliary flutes 122 are in middle (or central) regions of the surgical bur 120. As shown, the auxiliary flutes 122 include clearance surfaces 124 and rake surfaces 126 that are planar and semi-circular. Transition regions 128 between the clearance surfaces 124 and the rake surfaces 126 may extend parallel to or have a positive or negative taper angle relative to an axis-of-rotation 130. The auxiliary flutes 122 may be centered over an equator 132 of the surgical bur 120. Each of the auxiliary flutes 122, in the shown example, has a −10° radial rake angle, a 100° inside angle, a −5° (left-hand) flute axial angle, and has a clock angle such that the auxiliary flute is centered (or at a mid-point) between adjacent main flutes. This arrangement provides stability for cutting via regions of the surgical bur near a mid-line (or equator).

Figure 8:
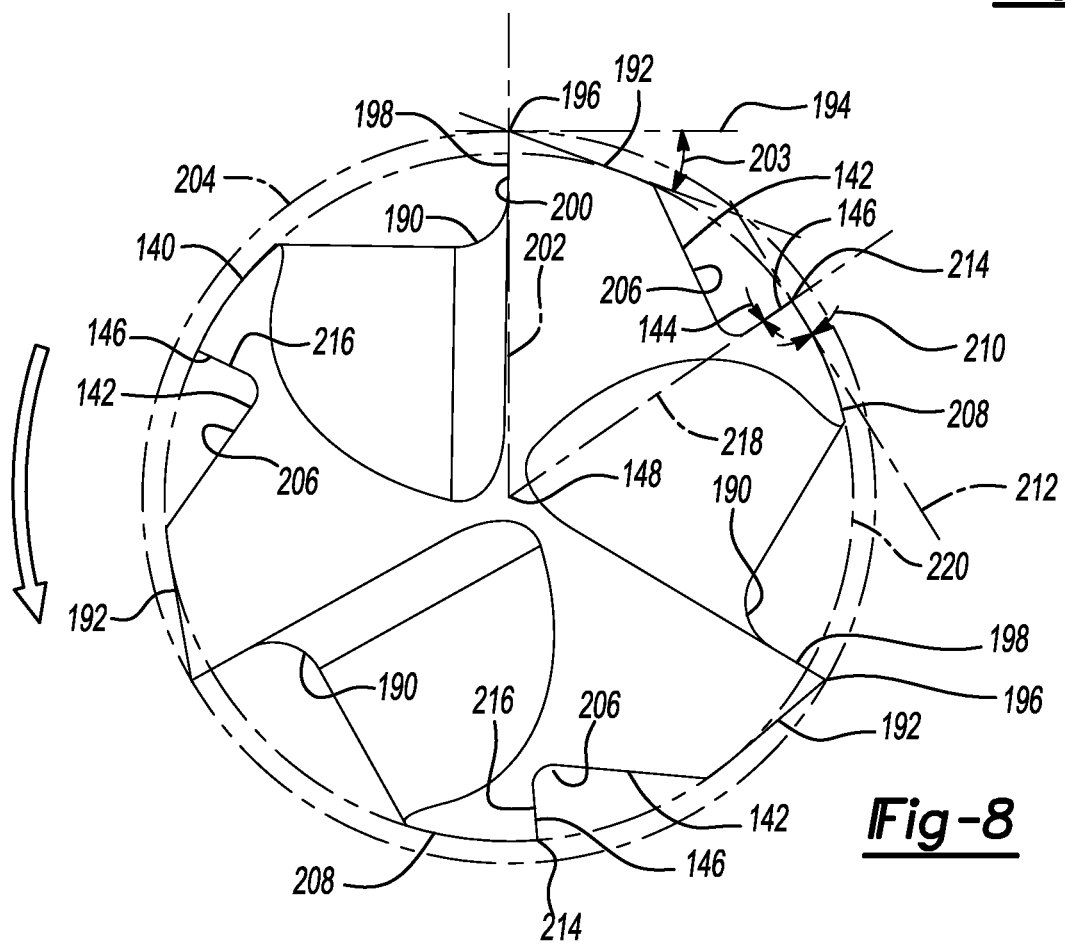
FIG. 8 is a distal end view of a ball style surgical bur incorporating auxiliary flutes with neutral radial rake angles in accordance with the present disclosure.
Figure 9:
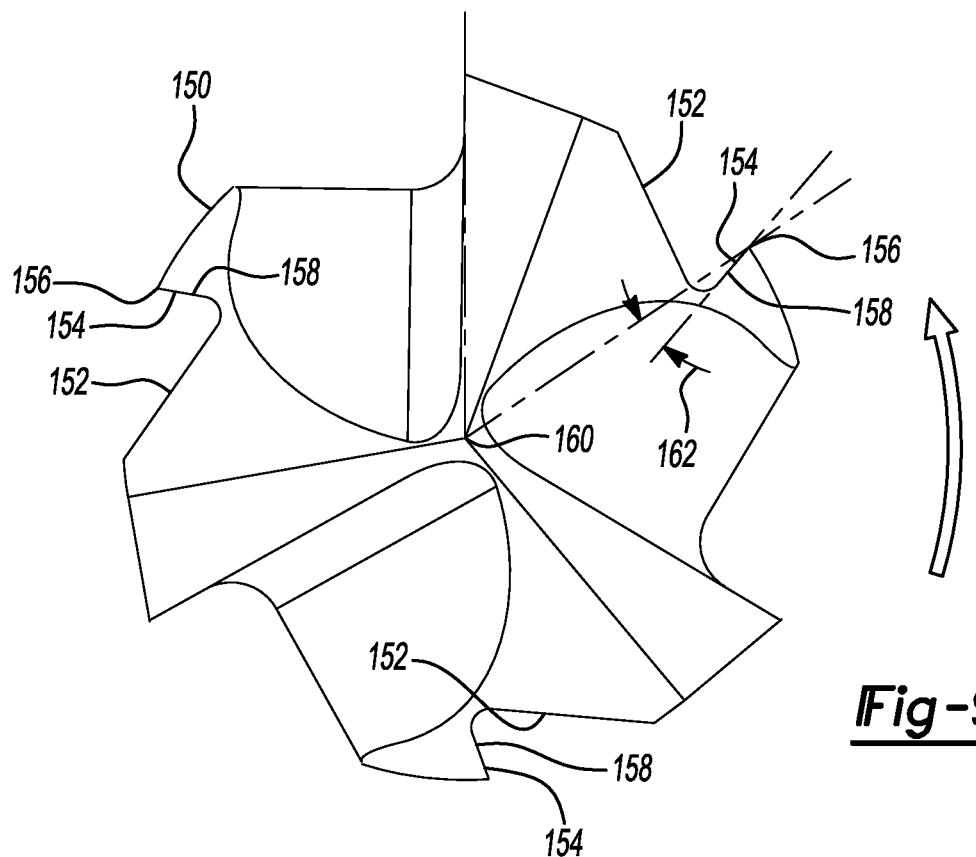
FIG. 9 is a distal end view of a ball style surgical bur incorporating auxiliary flutes with positive radial rake angles in accordance with the present disclosure.
Figure 10:
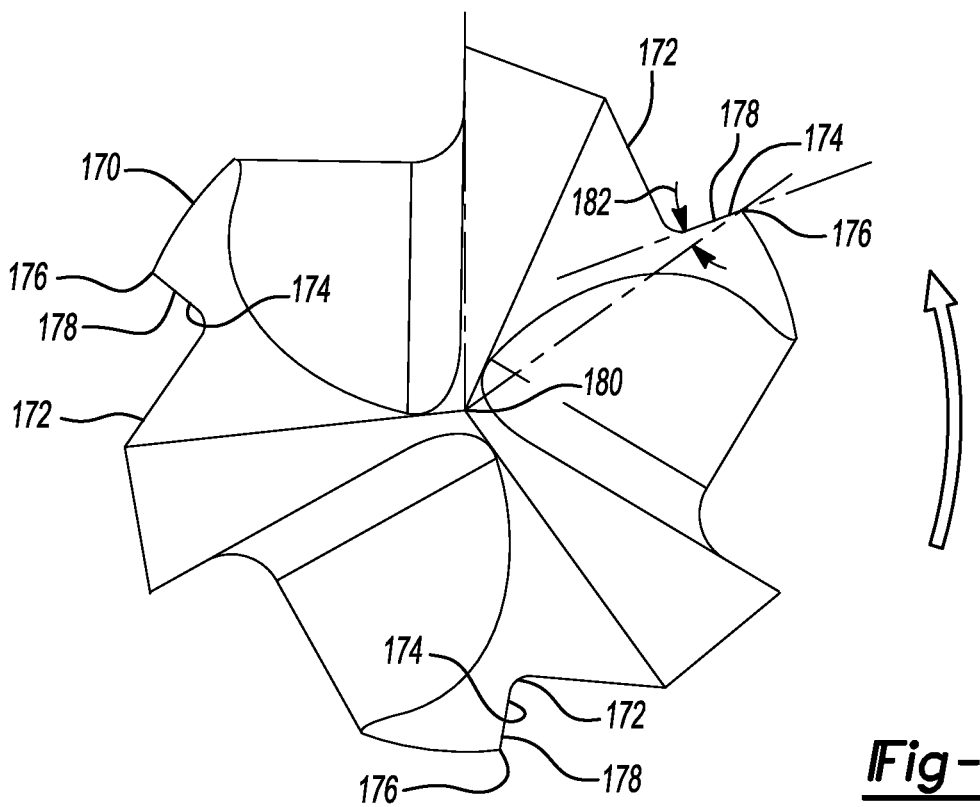
FIG. 10 is a distal end view of a ball style surgical bur incorporating auxiliary flutes with negative radial rake angles in accordance with the present disclosure.

FIGS. 8-10 show ball style surgical burs having auxiliary flutes with different radial rake angles. FIG. 8 shows a distal end view of a ball style surgical bur 140 incorporating auxiliary flutes 142 with neutral radial rake angles 144. Rake surfaces 146 of the auxiliary flutes 142 extend parallel to an axis-of-rotation (designated as point 148). Planes that respectively include the rake surfaces 146 extend through the axis-of-rotation 148.

FIG. 9 shows a distal end view of a ball style surgical bur 150 incorporating auxiliary flutes 152 with positive radial rake angles. Rake surfaces 154 of the auxiliary flutes 152, when viewed at the distal end of the surgical bur 150, are at positive rake angles relative to respective planes extending from outermost points 156 on cutting edges 158 of the rake surfaces 154 through an axis-of-rotation (designated as point 160). One of the positive rake angles is designated as 162. As shown, the positive rake angles are 15°. A positive radial rake angle can increase cutting efficiency.

FIG. 10 shows a distal end view of a ball style surgical bur 170 incorporating auxiliary flutes 172 with negative radial rake angles. Rake surfaces 174 of the auxiliary flutes 172, when viewed at the distal end of the surgical bur 170, are at negative rake angles relative to respective planes extending from outermost points 176 on cutting edges 178 of the rake surfaces 174 through an axis-of-rotation (designated as point 180). One of the positive rake angles is designated 182. As shown, the positive rake angles are −15°. A negative radial rake angle and a neutral radial rake angle can provide a stabilizing effect.

Different surgical instruments may have different working lengths (or distances from a grip (or motor housing) to (i) a cutting portion of the surgical tool, or (ii) a cutting portion of a corresponding surgical bur. Typically, the longer the working length and/or the longer an exposed length (distance from attachment to surgical bur), the less stable a surgical bur is during use.

Negative to neutral rake angles can provide a stabilizing effect, whereas positive rake angles can improve cutting efficiency. The auxiliary flutes disclosed herein may have positive, neutral and/or negative axial rake (or helix) angles.

Negative axial rake angles in the distal region (or tip) can provide a stabilizing effect, whereas positive radial rake angles at an equator or proximal region of a surgical bur can provide increased cutting efficiency. Incorporating auxiliary flutes with axial and/or radial rake angles that provide a stabilizing effect, allows for an exposed length of a corresponding surgical tool to be increased without negatively affecting stability while cutting. The increased instability associated with increasing the exposure length may be compensated for by the increased stability provided by the negative and/or neutral rake angles.

In the example shown in FIG. 8, main flutes 190 of the surgical bur 140 have primary relief surfaces 192 with positive relief angles. The relief angles of the primary relief surfaces 192 are measured between the relief surfaces 192 and tangential lines (one tangential line is designated 194) extending (i) through first outermost points 196 on the cutting edges 198 of rake surfaces 200 of the main flutes 190, and (ii) perpendicular to lines (one line is designated 202) extending between the first outermost points 196 and the axis-of-rotation 148. The relief angles (one relief angle is designated 203) of the primary relief surfaces 192 may be neutral or negative. The positive relief angles do not track a circle 204 extending through the first outermost points 196. The positive relief angles provide increased operating efficiency due to less surface (or tissue) contact and thus less drag. Clearance surfaces 206 (or secondary relief surfaces) of the auxiliary flutes 142 have higher positive relief angles than the relief angles of the primary relief surfaces 192.

The auxiliary flutes 142 have relief surfaces 208 that may have neutral relief angles (one relief angle is designated 210), as shown. The relief angles of the relief surfaces 208 are measured between the relief surfaces 208 and tangential lines (one tangential line is designated 212) extending (i) through second outermost points 214 on the cutting edges 216 of the rake surfaces 146, and (ii) perpendicular to lines (one line is designated 218) extending between the second outermost points 214 and the axis-of-rotation 148. The relief angles of the relief surfaces 208 of the auxiliary flutes 142 may be positive or negative. The neutral relief angles (i) track an inner circle 220 that extends through the second outermost points 214, and (ii) provide a stabilizing effect.

Figure 12:
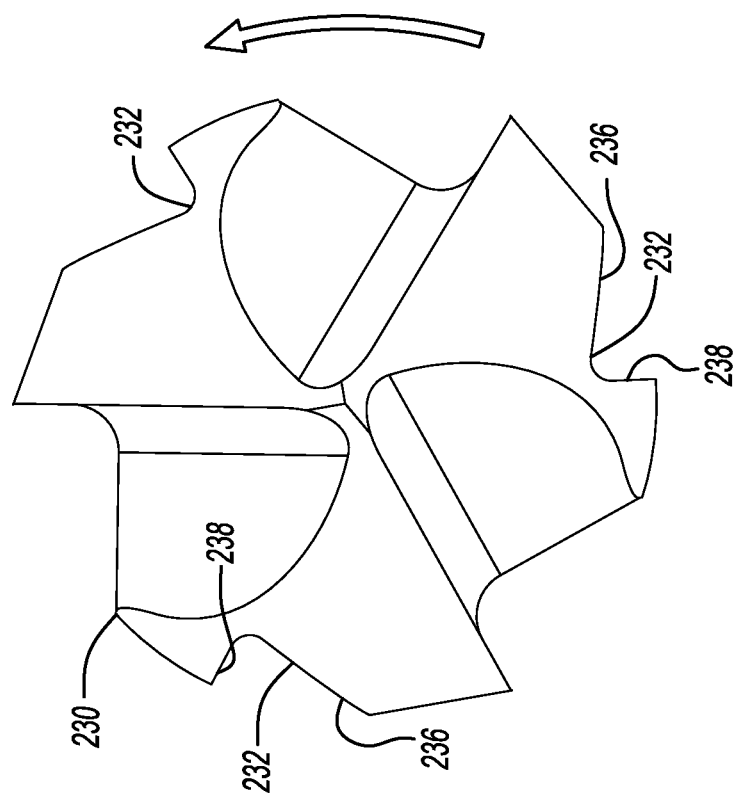
FIG. 12 is a distal end view of the ball style surgical bur of FIG. 11.
Figure 11:
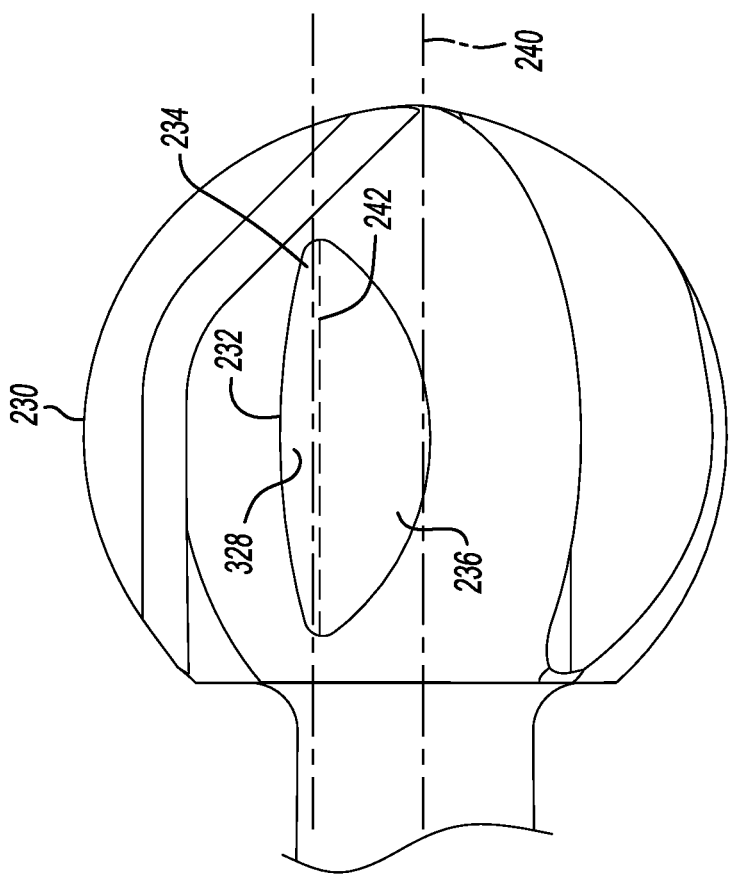
FIG. 11 is a radial side view of a ball style surgical bur illustrating auxiliary flutes with a neutral flute axial angle in accordance with the present disclosure.

FIGS. 11 and 12 show a ball style surgical bur 230 illustrating auxiliary flutes 232 with neutral flute axial angles. Transition regions 234 between clearance surfaces 236 and rake surfaces 238 of the auxiliary flutes 232 extend parallel to an axis-of-rotation 240. Put another way, transition lines (one transition line is designated 242) extending axially between the clearance surfaces 236 and the rake surfaces 238 are parallel to the axis-of-rotation 240. The transition lines may be parallel to or refer to edges of the clearance surfaces 236. The transition lines may be parallel to or refer to edges of the rake surfaces 238. As a result, flute axial angles of the auxiliary flutes 234 relative to the axis-of-rotation are 0°.

Figure 14:
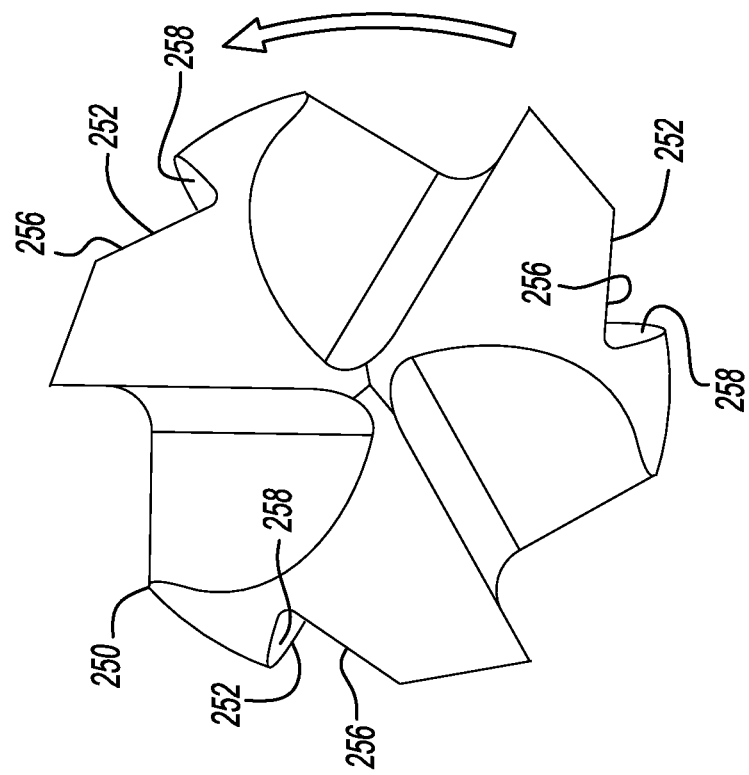
FIG. 14 is a distal end view of the ball style surgical bur of FIG. 13.
Figure 13:
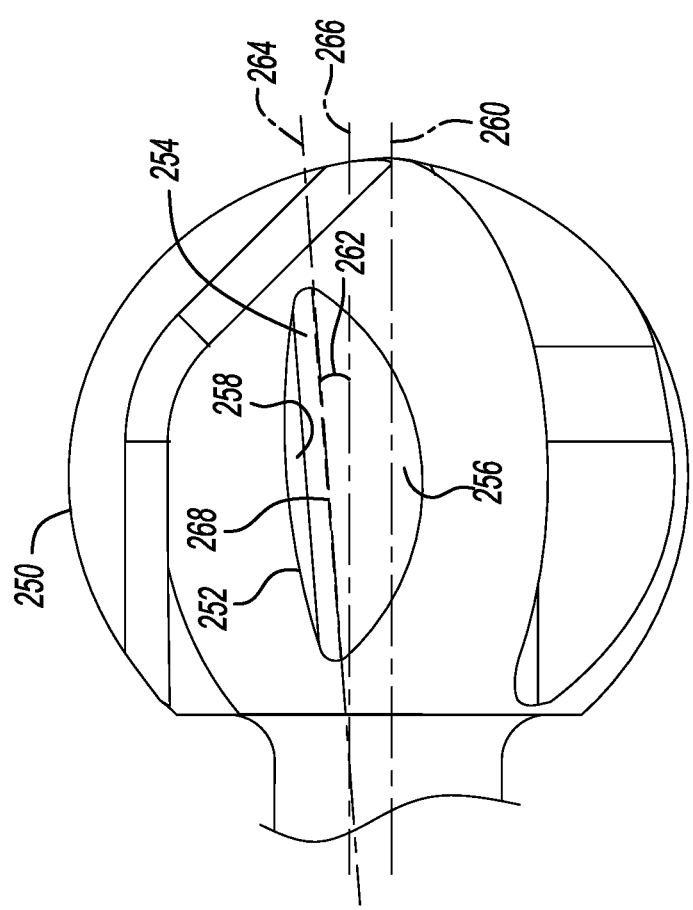
FIG. 13 is a radial side view of a ball style surgical bur illustrating auxiliary flutes with a left-hand flute axial angle in accordance with the present disclosure.

FIGS. 13 and 14 show a ball style surgical bur 250 illustrating auxiliary flutes 252 with left-hand flute axial angles. Transition regions 254 between clearance surfaces 256 and rake surfaces 258 of the auxiliary flutes 252 do not extend parallel to an axis-of-rotation 260 when viewed head-on (or from a direction directly opposite the corresponding transition region). A left-hand flute axial angle 262 is shown between lines 264, 266 that extend respectively parallel to (i) a transition line 268 extending in a corresponding one of the transition region 254 between one of the clearance surfaces 256 and one of the rake surfaces 258, and (ii) the axis-of-rotation 260. The transition line 268 may be parallel to or refer to an edge of the corresponding clearance surface. The transition line 268 may be parallel to or refer to an edge of the corresponding rake surface. In the example shown, the left-hand flute axial angle is 5°.

FIGS. 15 and 16 show a ball style surgical bur 270 illustrating auxiliary flutes 272 with right-hand flute axial angles. Transition regions 274 between clearance surfaces 276 and rake surfaces 278 of the auxiliary flutes 272 do not extend parallel to an axis-of-rotation 280 when viewed head-on. A right-hand flute axial angle 282 is shown between lines 284, 286 that extend respectively parallel to (i) a transition line 288 extending in one of the transition regions 274 between one of the clearance surfaces 276 and one of the rake surfaces 278, and (ii) the axis-of-rotation 280. The transition line 288 may be parallel to or refer to an edge of the corresponding clearance surface. The transition line may be parallel to or refer to an edge of the corresponding rake surface. In the example shown, the right-hand flute axial angle is 5°.

A flute axial angle may be set to improve stability and/or cutting efficiency. A radial rake angle is related to a flute axial angle, such that the radial rake angle may increase or decrease longitudinally along a length of the flute depending upon whether the flute axial angle is a left-hand flute axial angle or a right-hand flute axial angle. For example, a right-hand flute axial angle has a lowest corresponding rake angle at a distal end of the flute. The radial rake angle increases in size towards a proximal end of the flute.

Figure 17:
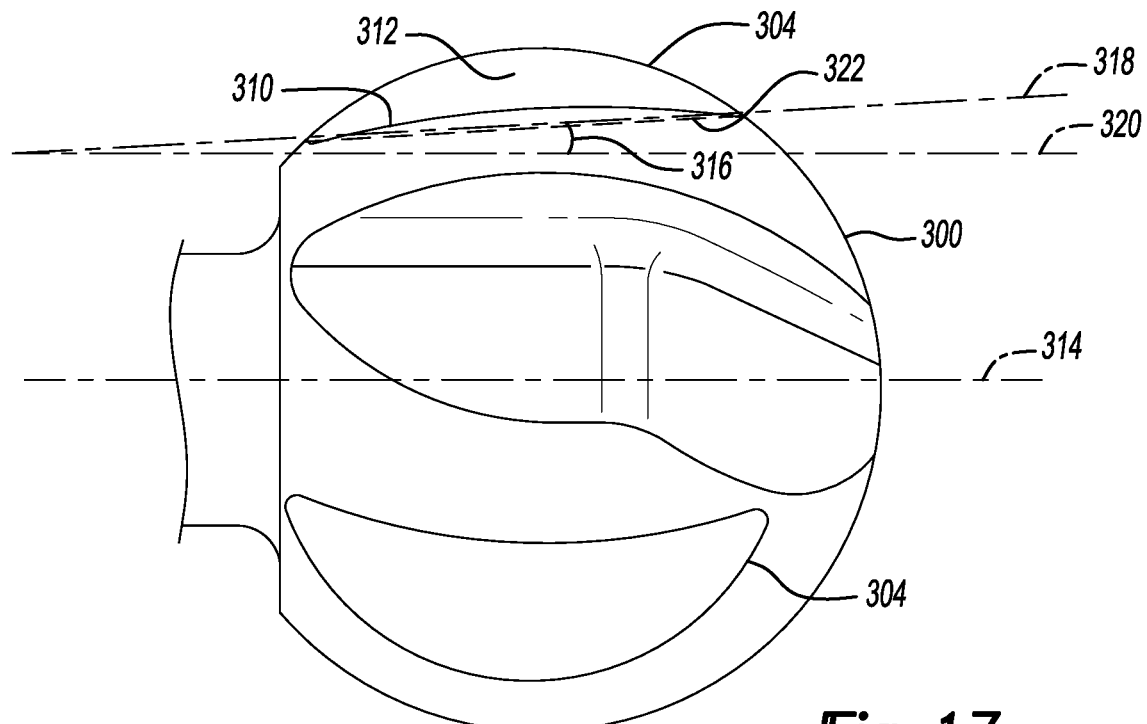
FIG. 17 is a radial side view of a ball style surgical bur illustrating auxiliary flutes having negative taper in accordance with the present disclosure.
Figure 18:
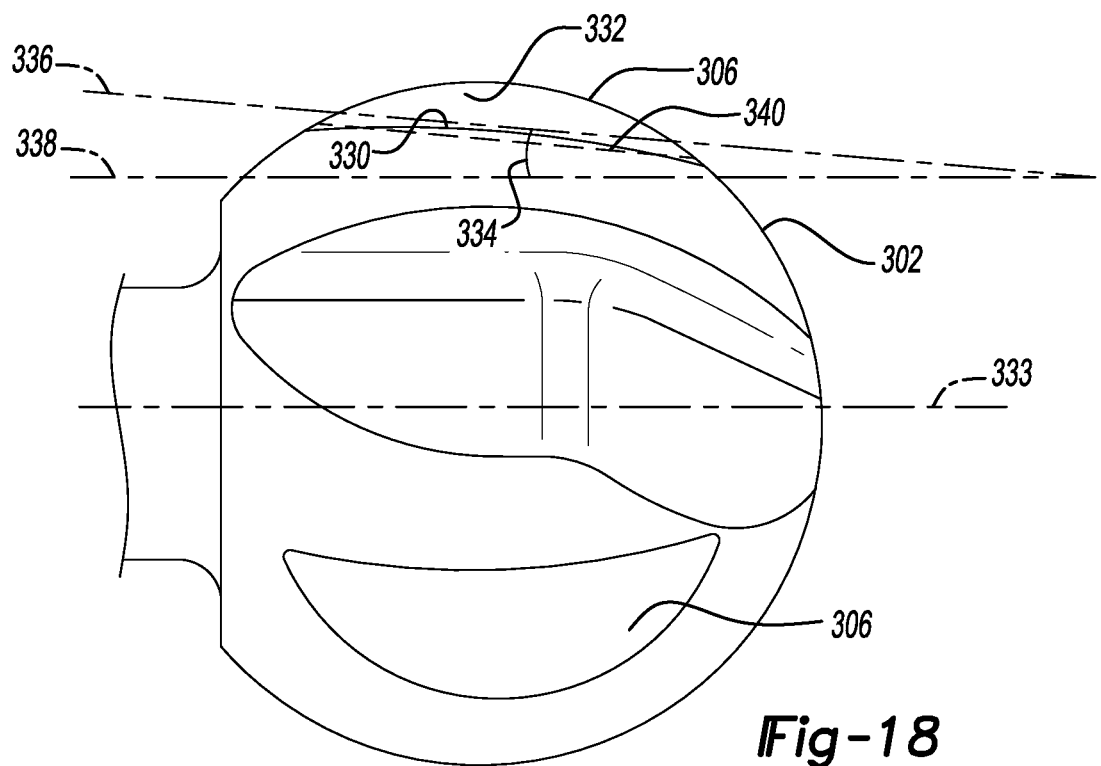
FIG. 18 is a radial side view of a ball style surgical bur illustrating auxiliary flutes having positive taper in accordance with the present disclosure.

FIGS. 17-18 show ball style surgical burs 300, 302 illustrating auxiliary flutes 304, 306 having negative and positive taper. The auxiliary flutes 304, 306 extend across corresponding equators of the surgical burs 300, 302. The auxiliary flutes 304, 306 may be centered on the equators (one half of each of the auxiliary flutes 304, 306 is located distal of the equator and the other half of each of the auxiliary flutes 304, 306 is located proximal to the equator). A larger portion of the auxiliary flutes 304, 306 may be located proximal to the equator, for example, when the auxiliary flutes 304, 306 have a negative taper. A larger portion of the auxiliary flutes 304, 306 may be located distal to the equator, for example, when the auxiliary flutes have positive taper. FIG. 17 shows the auxiliary flutes 304 having negative taper. Transition regions between clearance surfaces (one clearance surface is designated 310) and rake surfaces (one rake surface is designated 312) of the auxiliary flutes 304 do not extend parallel to an axis-of-rotation 314 when viewed radially from sides facing (or opposing) the corresponding rake surfaces. A taper angle 316 is shown between lines 318, 320 that extend respectively parallel to (i) a transition line 322 extending in a transition region between the clearance surface 310 and the rake surface 312, and (ii) the axis-of-rotation 314. The transition line 322 may be parallel to or refer to an edge of the clearance surface 310. The transition line 322 may be parallel to or refer to an edge of the rake surface 312.

FIG. 18 shows the auxiliary flutes 306 having positive taper. Transition regions between clearance surfaces (one of the clearance surfaces is designated 330) and rake surfaces (one of the rake surfaces is designated 332) of the auxiliary flutes 306 do not extend parallel to an axis-of-rotation 333 when viewed radially from sides facing (or opposing) the corresponding rake surfaces. A taper angle 334 is shown between lines 336, 338 that extend respectively parallel to (i) a transition line 340 extending in a transition region between the clearance surface 330 and the rake surface 332, and (ii) the axis-of-rotation 333. The transition line 340 may be parallel to or refer to an edge of the clearance surface 330. The transition line 340 may be parallel to or refer to an edge of the rake surface 332.

The taper angles of the auxiliary flutes disclosed herein may be set to locate the auxiliary flutes in regions of the corresponding surgical burs for predetermined stability and cutting effects. For example, a more positive taper moves the corresponding auxiliary flute towards a distal end of the corresponding surgical bur. A more negative taper moves the corresponding auxiliary flute towards a proximal end of the corresponding surgical bur.

Figure 19:
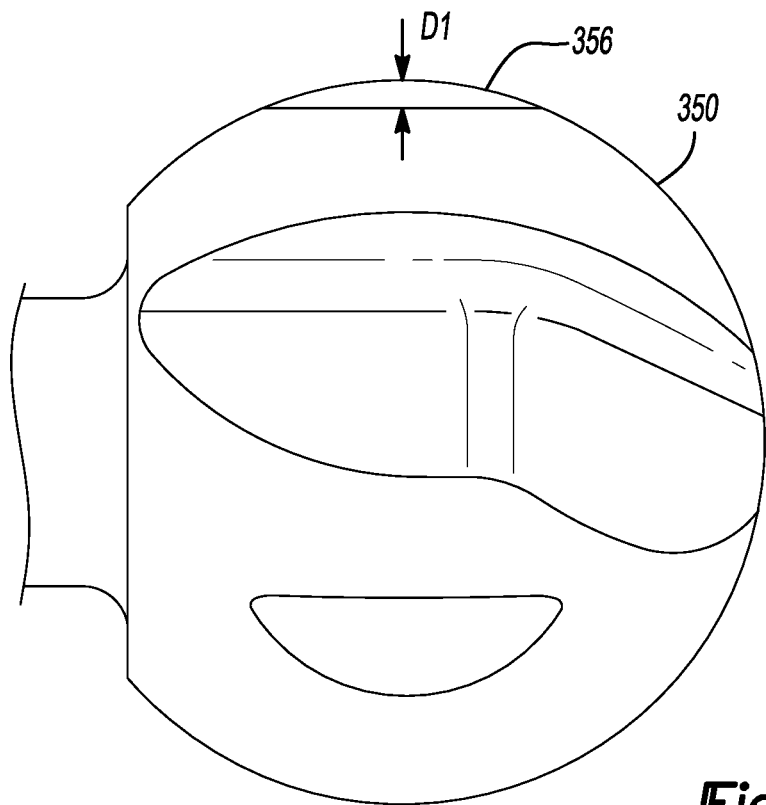
FIG. 19 is a radial side view of a ball style surgical bur having shallow auxiliary flutes in accordance with the present disclosure.
Figure 20:
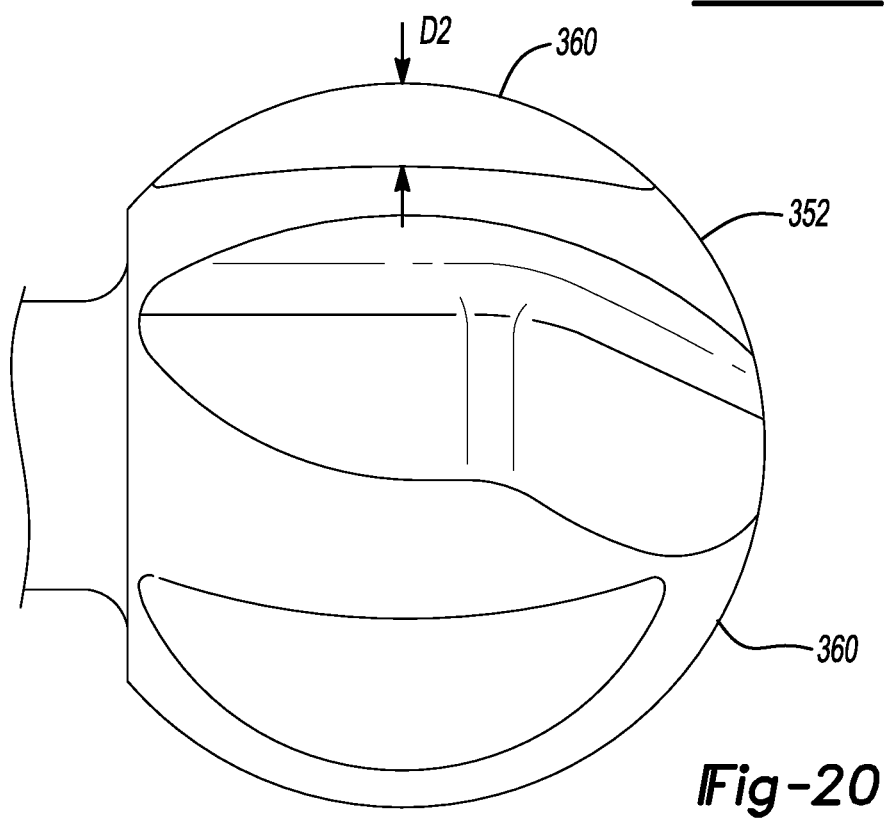
FIG. 20 is a radial side view of a ball style surgical bur having deep auxiliary flutes in accordance with the present disclosure.
Figure 23:
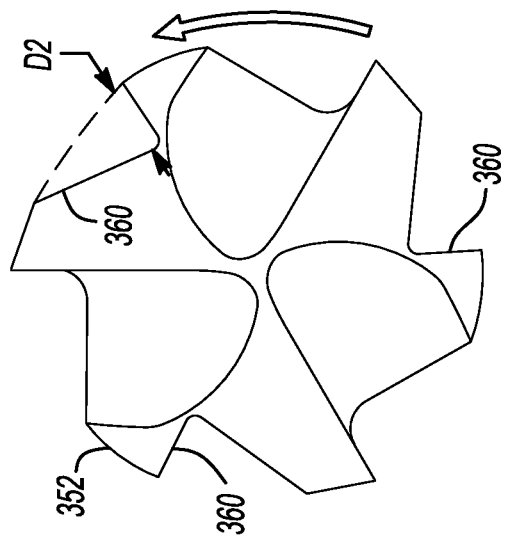
FIG. 23 is a distal end view of the ball style surgical bur of FIG. 20 in accordance with the present disclosure.
Figure 22:
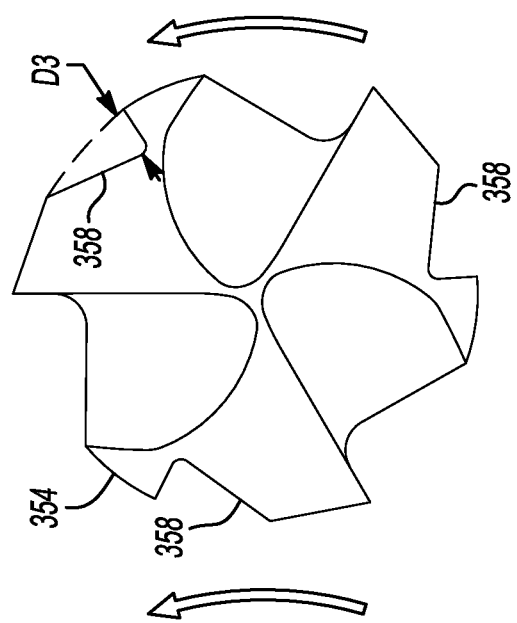
FIG. 22 is a distal end view of the ball style surgical bur having auxiliary flutes with an intermediate depth in accordance with the present disclosure.
Figure 21:
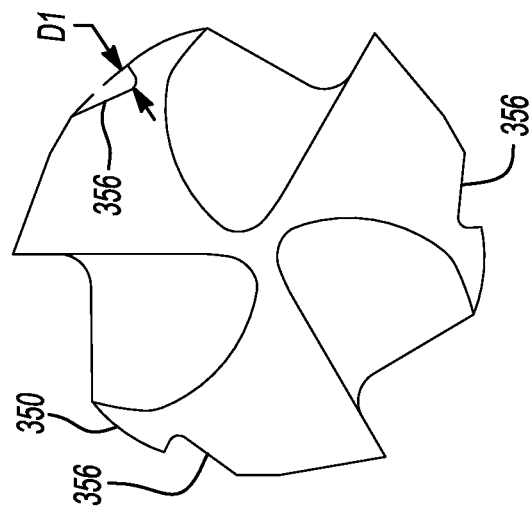
FIG. 21 is a distal end view of the ball style surgical bur of FIG. 19 in accordance with the present disclosure.

FIGS. 19-23 illustrate ball style surgical burs 350, 352, 354 having auxiliary flutes 356, 358, 360 with different depths D1, D2, D3. FIGS. 19 and 21 show the surgical bur 350 with the auxiliary flutes 356 that have the shallow depth D1 (a depth less than or equal to a first predetermined depth). FIGS. 20 and 23 show the surgical bur 352 with the auxiliary flutes 360 that have the deep depth D2 (a depth greater than or equal to the second predetermined depth). FIG. 22 shows the surgical bur 354 with the auxiliary flutes 360 with an intermediate depth D3 (a depth within a predetermined range that is greater than the first predetermined depth and less than a second predetermined depth). The depth D3 is greater than the depth D2, which is greater than the depth D1. The depth of an auxiliary flute refers to how far into a surgical bur the auxiliary flute is cut relative to (i) a corresponding relief surface of a main flute, and/or (ii) a relief surface of the auxiliary flute. Length (or surface area) of an auxiliary flute and how much (or magnitude at which) a flute affects surgical tool performance are based on a depth of the auxiliary flute. In general, the deeper the auxiliary flute the longer the auxiliary flute. Also, deeper auxiliary flutes tend to move clearance surfaces (non-cutting surfaces) of the auxiliary flutes closer to adjacent main flutes, which increase sizes of "bites" of the auxiliary flutes and as a result increase cutting efficiency.

FIGS. 24-26 illustrate ball style surgical burs 370, 372, 374 with auxiliary flutes 376, 378, 380 having corresponding inside flute angles 382, 384, 386. The inside flute angles 382, 384, 386 refer to angles between clearance surfaces 390, 392, 394 and respective rake surfaces 396, 398, 400 of the auxiliary flutes 376, 378, 380. FIG. 24 shows the ball style surgical bur 370 illustrating the first inside flute angle 382 (e.g., 60°). FIG. 25 shows the ball style surgical bur 372 illustrating the second inside flute angle 384 (e.g., 90°). FIG. 26 shows the ball style surgical bur 374 illustrating a shallow auxiliary flute with the third inside flute angle 386 and a particular radial rake angle (e.g., −20°).

Similar to depths of auxiliary flutes, inside flute angles can be adjusted to move clearance surfaces (non-cutting surfaces) of the auxiliary flutes towards cutting edges of adjacent main flutes. The larger the inside flute angles the closer the clearance surfaces of the auxiliary flutes are to the cutting edges of the adjacent main flutes. Also, similar to depths of auxiliary flutes, inside flute angles move where non-cutting surfaces of the auxiliary flutes intersect a tool surface (e.g., a relief surface of a main flute). The inside flute angles may be maintained at constant values while radial rake angles and flute depths are changed.

FIGS. 27-29 illustrate ball style surgical burs 410, 412, 414 having auxiliary flutes 416, 418, 420 having different clock angles 422, 424, 426. The clock angles 422, 424, 426 refer to, when viewing the auxiliary flutes 416, 418, 420 at a distal end of the surgical burs 410, 412, 414, angular positions of the auxiliary flutes 416, 418, 420 relative to respective adjacent main flutes 430, 432, 434. The clock angles indicate (i) angular distances about axis-of-rotations 436, 438, 440 between the main flutes 430, 432, 434 and the auxiliary flutes 416, 418, 420, and (ii) widths of primary relief surfaces 442, 444, 446 between the main flutes 430, 432, 434 and the auxiliary flutes 416, 418, 420.

FIG. 27 shows a distal end view of the ball style surgical bur 410 having the auxiliary flutes 416 with 35° clock angles. FIG. 28 shows a distal end view of the ball style surgical bur 412 having the auxiliary flutes 418 with 50° clock angles. FIG. 29 shows a distal end view of the ball style surgical bur 414 having the auxiliary flutes 420 with 70° clock angles.

Clock angles locate auxiliary flutes relative to main flutes at positions about an axis-of-rotation of the corresponding surgical bur. If the auxiliary flutes (first auxiliary flutes) have small clock angles or large clock angles, additional (or second) auxiliary flutes may be incorporated between the first auxiliary flutes and the corresponding main flutes. For example, a ball style surgical tool may include both the auxiliary flutes of FIG. 27 and the auxiliary flutes of FIG. 29. The clocking angles (or clocking positions) affect how much (or magnitude at which) the auxiliary flutes affect stability and/or cutting performance.

In the following FIGS. 30-35, ball style surgical burs 450, 452, 454 are disclosed with auxiliary flutes 458, 460, 462 located in distal regions and proximate to tips 464, 466, 468 of the surgical burs 450, 452, 454. In these locations, the auxiliary flutes 458, 460, 462 have radial rake angles and axial rake angles. The radial rake angles affect lateral cutting and the axial rake angles affect distal cutting of the surgical burs 450, 452, 454.

Figure 30:
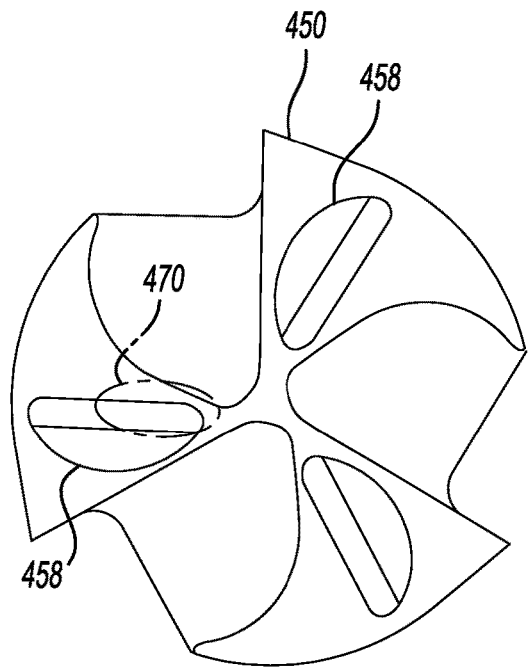
FIG. 30 is a distal end view of a ball style surgical bur illustrating auxiliary flutes with neutral axial rake angles in accordance with the present disclosure.
Figure 31:
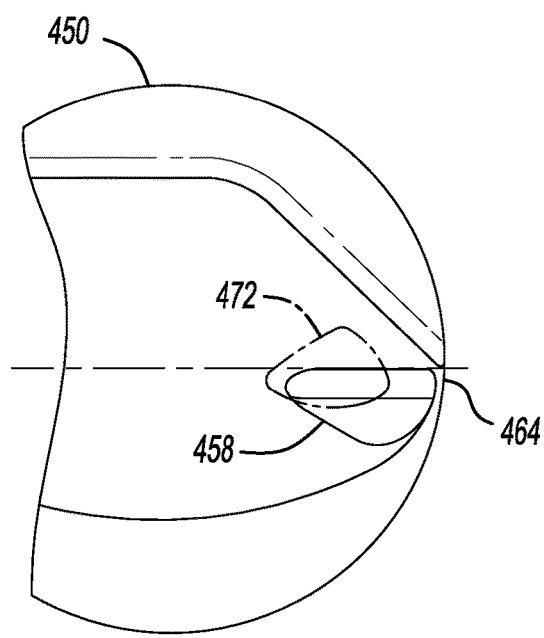
FIG. 31 is a radial side view of the ball style surgical bur of FIG. 30 and illustrating auxiliary flutes with neutral radial rake angles.

FIGS. 30-31 show the ball style surgical bur 450 illustrating the auxiliary flutes 458 with neutral rake angles (0°). FIG. 30 shows a distal end view of the surgical bur 450 and illustrates the auxiliary flutes 458 with neutral axial (or helix) rake angles. A circled dashed line region 470 indicates a portion of a corresponding auxiliary flute with an effective axial rake component. FIG. 31 shows a radial side view of the ball style surgical bur 450 and illustrates the auxiliary flutes 458 with neutral radial rake angles. A circled dashed line region 472 indicates a portion of a corresponding auxiliary flute with an effective radial rake component.

Figure 32:
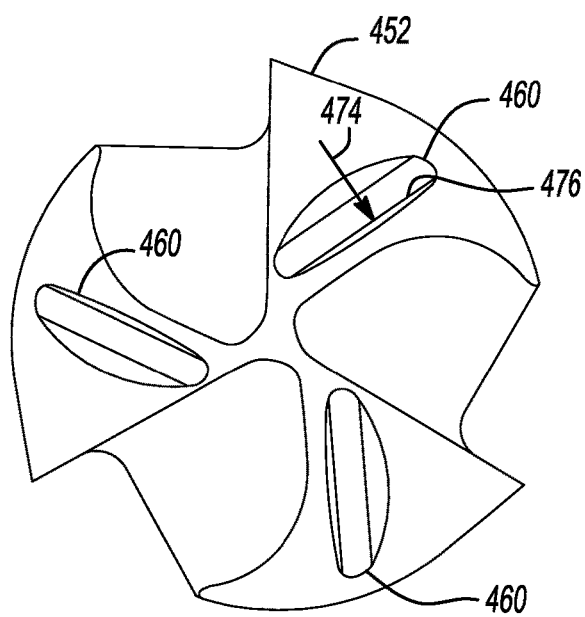
FIG. 32 is a distal end view of a ball style surgical bur illustrating auxiliary flutes with negative axial rake angles in accordance with the present disclosure.
Figure 33:
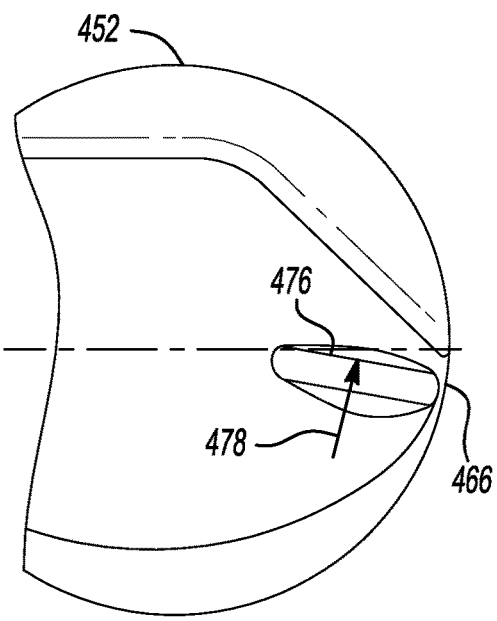
FIG. 33 is a radial side view of the ball style surgical bur of FIG. 32 and illustrating auxiliary flutes with negative radial rake angles.

FIGS. 32-33 show the ball style surgical bur 452 illustrating the auxiliary flutes 460 with negative rake angles. FIG. 32 shows a distal end view of the ball style surgical bur 452 and illustrates the auxiliary flutes 460 with negative axial rake angles. An arrow 474 indicates a portion of a corresponding auxiliary flute with a rake surface 476 that is exposed when viewed from a distal end or tip 466 of the surgical bur 452. Exposure of rake surfaces of the auxiliary flutes 460 is increased over that shown in FIG. 30, which indicates magnitude of the negative axial rake of the auxiliary flutes 460. FIG. 33 shows a radial side view of the ball style surgical bur 452 and illustrates the auxiliary flutes 460 with negative radial rake angles. An arrow 478 indicates a portion of a corresponding auxiliary flute with the rake surface 476 that is exposed when viewed radially. As shown, the auxiliary flutes 460 have increased rake surface exposure over the rake surfaces of the auxiliary flutes 458 of FIG. 31, illustrating the negative radial rake of the auxiliary flutes 460.

Figure 34:
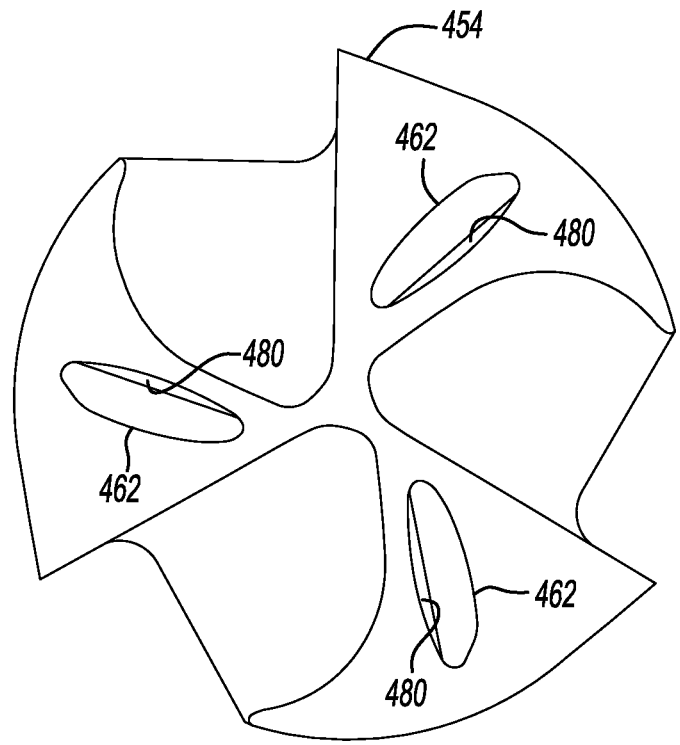
FIG. 34 is a distal end view of a ball style surgical bur illustrating auxiliary flutes with negative axial rake angles in accordance with the present disclosure.
Figure 35:
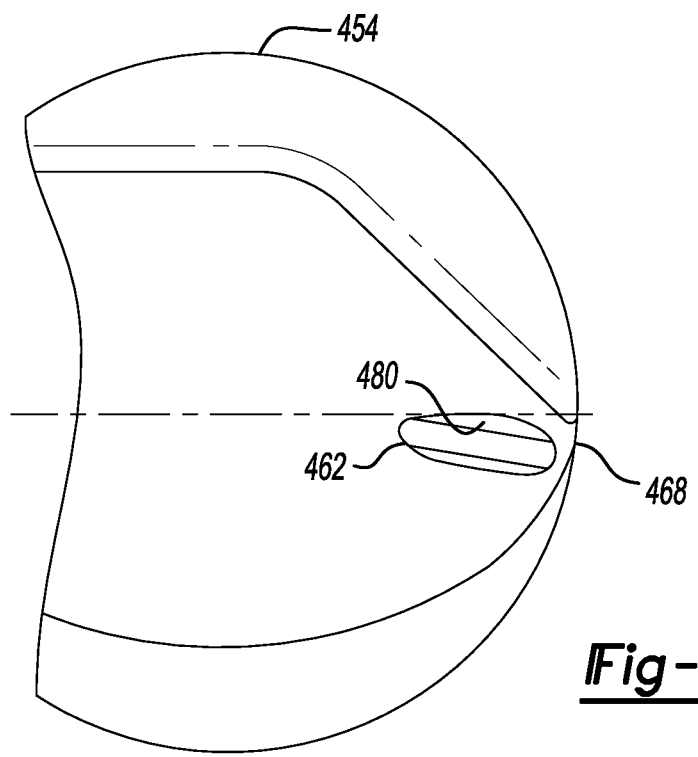
FIG. 35 is a radial side view of the ball style surgical bur of FIG. 34 and illustrating auxiliary flutes with negative radial rake angles.

FIGS. 34-35 show the ball style surgical bur 454 illustrating the auxiliary flutes 462 with negative rake angles. The rake angles of the ball style surgical bur 454 are more negative than the rake angles of the ball style surgical bur 452 of FIGS. 32-33. FIG. 34 shows a distal end view of the ball style surgical bur 454 and illustrates the auxiliary flutes 462 with negative axial rake angles. Exposure of rake surfaces 480 of the auxiliary flutes 462 is increased over that shown in FIG. 32, which indicates magnitude of the negative axial rake of the auxiliary flutes 462. The auxiliary flutes 462 have a left-hand flute axial angle which manifested the increase in negative axial rake over the auxiliary flutes 460 of FIG. 32. FIG. 35 shows a radial side view of the ball style surgical bur 454 and illustrates the auxiliary flutes 462 with negative radial rake angles. As shown, the auxiliary flutes 462 have increased rake surface exposure over the rake surfaces of the auxiliary flutes 460 of FIG. 33, illustrating the increased negative radial rake of the auxiliary flutes 462.

Auxiliary flute features are described above that are localized on surgical burs to augment cutting performance for particular uses during, for example, dissection. Auxiliary flutes and/or flute features are disclosed as being localized in a distal region, a middle region (or near an equator), and/or a proximal region of a surgical bur. The auxiliary flutes may transition between regions of the surgical bur, such that the auxiliary flutes provide a certain feature in a first region and a different feature in a second region. The auxiliary flutes do not extend continuously from a proximal end of a surgical bur to a tip (or distal end) of the surgical bur. The disclosed features provide numerous surgical bur geometries that may be incorporated into a surgical bur to achieve requirements for cutting efficiency and/or cutting stability.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical bur for use in cutting bone, comprising:
 a plurality of primary cutting flutes including (i) first clearance surfaces and (ii) first rake surfaces having first bone cutting edges; and
 a plurality of auxiliary cutting flutes including (i) second clearance surfaces and (ii) second rake surfaces having second bone cutting edges,
 wherein at least one of the plurality of auxiliary cutting flutes has a selected clock angle relative to one of the plurality of primary cutting flutes of at least 35°, and
 wherein at least a first auxiliary cutting flute of the plurality of cutting flutes is discretely located on a proximal region of the surgical bur and at least a second auxiliary cutting flute of the plurality of cutting flutes is discretely located on a distal region of the surgical bur, the proximal and distal regions of the surgical bur separated by a planar portion defined where a diameter of the surgical bur is at a maximum, and wherein each of the auxiliary cutting flutes of the plurality of auxiliary cutting flutes remains spaced relative to the planar portion in a respective region.

2. The surgical bur of claim 1, wherein each of the plurality of auxiliary cutting flutes has the selected clock angle relative to one of the plurality of primary cutting flutes that is at least 50°.

3. The surgical bur of claim 1, wherein each of the plurality of auxiliary cutting flutes has the selected clock angle relative to one of the plurality of primary cutting flutes that is at least 70°.

4. The surgical bur of claim 1, further comprising at least one additional auxiliary cutting flute configured to transition between the proximal and distal regions of the surgical bur, such that the at least one additional auxiliary cutting flute provides a first feature in a first region and a second feature in a second region, wherein the first feature is different than the second feature.

5. The surgical bur of claim 1, wherein the clock angle indicates an angular distance about an axis-of-rotation of the surgical bur between one flute of the plurality of primary cutting flutes and one auxiliary cutting flute of the plurality of auxiliary cutting flutes.

6. The surgical bur of claim 5, wherein the clock angle further indicates a width of a primary relief surfaces between one flute of the plurality of primary cutting flutes and one auxiliary cutting flute of the plurality of auxiliary cutting flutes.

7. A surgical bur for use in cutting bone, comprising:
a plurality of primary cutting flutes including first rake surfaces having first bone cutting edges; and
a plurality of auxiliary cutting flutes including second rake surfaces having second bone cutting edges,
wherein each auxiliary cutting flute of the plurality of auxiliary cutting flutes has a clock angle such that each auxiliary cutting flute of the plurality of auxiliary cutting flutes is centered between adjacent primary cutting flutes, and
wherein at least a first auxiliary cutting flute of the plurality of cutting flutes is discretely located on a proximal region of the surgical bur and at least a second auxiliary cutting flute of the plurality of cutting flutes is discretely located on a distal region of the surgical bur, the proximal and distal regions of the surgical bur separated by a planar portion defined where a diameter of the surgical bur is at a maximum, and wherein each of the auxiliary cutting flutes of the plurality of auxiliary cutting flutes remains spaced relative to the planar portion in a respective region.

8. The surgical bur of claim 7, wherein the arrangement of the plurality of auxiliary cutting flutes relative to the plurality of primary cutting flutes provides stability for cutting near a bur equator.

9. The surgical bur of claim 7, wherein each of the plurality of auxiliary cutting flutes includes a selected clock angle relative to one of the plurality of primary cutting flutes of at least 35° to 70°.

10. The surgical bur of claim 7, wherein at least one auxiliary cutting flute of the plurality of auxiliary cutting flutes is located between a pair of adjacent ones of the plurality of primary cutting flutes.

11. A surgical bur for use in cutting bone, comprising:
a plurality of primary cutting flutes including (i) first clearance surfaces and (ii) first rake surfaces having first bone cutting edges; and
a plurality of auxiliary cutting flutes including (i) second clearance surfaces and (ii) second rake surfaces having second bone cutting edges,
wherein at least one of the plurality of auxiliary cutting flutes has a transition region that extends non-radially from an axis of rotation of the surgical bur, and
wherein at least a first auxiliary cutting flute of the plurality of cutting flutes is discretely located on a proximal region of the surgical bur and at least a second auxiliary cutting flute of the plurality of cutting flutes is discretely located on a distal region of the surgical bur, the proximal and distal regions of the surgical bur separated by a planar portion defined where a diameter of the surgical bur is at a maximum, and wherein each of the auxiliary cutting flutes of the plurality of auxiliary cutting flutes remains spaced relative to the planar portion in a respective region.

12. The surgical bur of claim 11, wherein the transition region of the at least one of the plurality of auxiliary cutting flutes is between the second clearance surface and the second rake surface.

13. The surgical bur of claim 11, wherein the transition region of the at least one of the plurality of auxiliary cutting flutes is concave-shaped.

14. The surgical bur of claim 11, wherein the second clearance surface and the second rake surface each include respective cutting edges.

15. The surgical bur of claim 11, wherein at least another one auxiliary cutting flute of the plurality of auxiliary cutting flutes has a radial transition region that extends radially from the axis of rotation of the surgical bur;
wherein the radial transition region of the at least another one auxiliary cutting flute of the plurality of auxiliary cutting flutes is between the second clearance surface and the second rake surface.

16. The surgical bur of claim 11, wherein the at least one of the plurality of auxiliary cutting flutes includes at least a first auxiliary cutting flute and a second auxiliary cutting flute;
wherein the first auxiliary cutting flute and the second auxiliary cutting flute share the transition region.

* * * * *